United States Patent
Passerini et al.

(10) Patent No.: US 11,589,924 B2
(45) Date of Patent: Feb. 28, 2023

(54) NON-INVASIVE ASSESSMENT AND THERAPY GUIDANCE FOR CORONARY ARTERY DISEASE IN DIFFUSE AND TANDEM LESIONS

(71) Applicant: Siemens Healthcare GmbH, Erlangen (DE)

(72) Inventors: Tiziano Passerini, Plainsboro, NJ (US); Thomas Redel, Poxdorf (DE); Paul Klein, Princeton, NJ (US); Lucian Mihai Itu, Brasov (RO); Saikiran Rapaka, Pennington, NJ (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 514 days.

(21) Appl. No.: 16/620,272

(22) PCT Filed: Jul. 26, 2018

(86) PCT No.: PCT/EP2018/070254
§ 371 (c)(1),
(2) Date: Dec. 6, 2019

(87) PCT Pub. No.: WO2019/025270
PCT Pub. Date: Feb. 7, 2019

(65) Prior Publication Data
US 2021/0085397 A1    Mar. 25, 2021

Related U.S. Application Data

(60) Provisional application No. 62/539,575, filed on Aug. 1, 2017.

(30) Foreign Application Priority Data

Aug. 1, 2017  (EP) .................................... 17465533

(51) Int. Cl.
A61B 5/00     (2006.01)
A61B 34/10    (2016.01)
(Continued)

(52) U.S. Cl.
CPC .............. *A61B 34/10* (2016.02); *A61B 5/026* (2013.01); *A61B 5/4887* (2013.01);
(Continued)

(58) Field of Classification Search
CPC combination set(s) only.
See application file for complete search history.

(56) References Cited

U.S. PATENT DOCUMENTS 6,236,878 B1   5/2001  Taylor et al.
7,860,290 B2   12/2010 Gulsun et al.
(Continued)

FOREIGN PATENT DOCUMENTS

WO    WO2016075331 A2    5/2016
WO    WO2017093337 A1    6/2017
WO    WO2017187269 A1    11/2017

OTHER PUBLICATIONS

C. A. Taylor, et al., "Open Problems in Computational Vascular Biomechanics: Hemodynamics and Arterial Wall Mechanics," Comput Methods Appl Meeh. Eng., vol. 198, pp. 3514-3523, 2009.
(Continued)

*Primary Examiner* — Joel F Brutus

(57) ABSTRACT

A method and system for non-invasive assessment and therapy planning for coronary artery disease from medical image data of a patient is disclosed. Geometric features representing at least a portion of a coronary artery tree of the patient are extracted from medical image data. Lesions are detected in coronary artery tree of the patient and a hemodynamic quantity of interest is computed at a plurality of points along the coronary artery tree including multiple
(Continued)

points within the lesions based on the extracted geometric features using a machine learning model, resulting in an estimated pullback curve for the hemodynamic quantity of interest. Post-treatment values for the hemodynamic quantity of interest are predicted at the plurality of points along the coronary artery tree including the multiple points within the lesions for each of one or more candidate treatment options for the patient, resulting in a respective predicted post-treatment pullback curve for the hemodynamic quantity of interest for each of the one or more candidate treatment options. A visualization of a treatment prediction for at least one of the candidate treatment options is displayed.

24 Claims, 13 Drawing Sheets

(51) Int. Cl.
  *G16H 30/20* (2018.01)
  *G16H 30/40* (2018.01)
  *G16H 50/20* (2018.01)
  *G16H 50/70* (2018.01)
  *G16H 20/40* (2018.01)
  *G16H 50/50* (2018.01)
  *G16H 50/30* (2018.01)
  *G06N 3/08* (2023.01)
  *G06N 3/04* (2023.01)
  *G06T 7/00* (2017.01)
  *A61B 5/026* (2006.01)

(52) U.S. Cl.
  CPC .......... *A61B 5/7267* (2013.01); *A61B 5/7278* (2013.01); *G06N 3/0445* (2013.01); *G06N 3/0454* (2013.01); *G06N 3/08* (2013.01); *G06T 7/0012* (2013.01); *G16H 20/40* (2018.01); *G16H 30/20* (2018.01); *G16H 30/40* (2018.01); *G16H 50/20* (2018.01); *G16H 50/30* (2018.01); *G16H 50/50* (2018.01); *G16H 50/70* (2018.01); *A61B 2034/104* (2016.02); *A61B 2034/105* (2016.02); *A61B 2034/107* (2016.02); *G06T 2207/20081* (2013.01); *G06T 2207/20084* (2013.01); *G06T 2207/30048* (2013.01); *G06T 2207/30096* (2013.01); *G06T 2207/30101* (2013.01)

(56) References Cited

U.S. PATENT DOCUMENTS

| | | |
|---|---|---|
| 7,953,266 B2 | 5/2011 | Gulsun et al. |
| 8,098,918 B2 | 1/2012 | Zheng et al. |
| 8,157,742 B2 | 4/2012 | Taylor |
| 8,200,466 B2 | 6/2012 | Spilker et al. |
| 8,249,815 B2 | 8/2012 | Taylor |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| 8,386,188 B2 | 2/2013 | Taylor et al. |
| 9,195,801 B1 | 11/2015 | Sankaran et al. |
| 9,349,178 B1 | 5/2016 | Itu et al. |
| 9,747,525 B2 | 8/2017 | Sauer et al. |
| 9,918,690 B2 | 3/2018 | Itu et al. |
| 2010/0017171 A1 | 1/2010 | Spilker et al. |
| 2010/0067760 A1 | 3/2010 | Zhang et al. |
| 2011/0224542 A1 | 9/2011 | Mittal et al. |
| 2012/0022843 A1 | 1/2012 | Tonasec et al. |
| 2012/0041301 A1 | 2/2012 | Redel |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0072190 A1 | 3/2012 | Sharma et al. |
| 2012/0121151 A1 | 5/2012 | Bernhardt et al. |
| 2012/0150516 A1 | 6/2012 | Taylor et al. |
| 2012/0203530 A1 | 8/2012 | Sharma et al. |
| 2012/0243761 A1 | 9/2012 | Senzig et al. |
| 2013/0054214 A1 | 2/2013 | Taylor |
| 2013/0064438 A1 | 3/2013 | Taylor et al. |
| 2013/0132054 A1 | 5/2013 | Sharma et al. |
| 2013/0246034 A1 | 9/2013 | Sharma et al. |
| 2014/0058715 A1 | 2/2014 | Sharma et al. |
| 2015/0112182 A1 | 4/2015 | Sharma et al. |
| 2015/0324962 A1 | 11/2015 | Itu et al. |
| 2015/0374243 A1 | 12/2015 | Itu et al. |
| 2016/0022371 A1* | 1/2016 | Sauer ..................... G16H 30/40 600/407 |
| 2016/0042144 A1* | 2/2016 | Sankaran ................ A61B 34/10 703/11 |
| 2016/0048972 A1* | 2/2016 | Kam ..................... G06T 7/0016 382/128 |
| 2016/0157807 A1* | 6/2016 | Anderson ............ A61B 6/4417 600/407 |
| 2016/0166209 A1 | 6/2016 | Itu et al. |
| 2016/0196384 A1 | 7/2016 | Mansi et al. |
| 2017/0032097 A1 | 2/2017 | Itu et al. |
| 2017/0245821 A1 | 8/2017 | Itu et al. |
| 2017/0293735 A1 | 10/2017 | Itu et al. |
| 2017/0329905 A1 | 11/2017 | Passerini et al. |
| 2018/0322366 A1* | 11/2018 | Lim ..................... G06V 10/82 |

OTHER PUBLICATIONS

Chamuleau er al., "Association between coronary lesion severity and distal microvascular resistance in patients with coronary artery disease," Am J Physiol Heart Circ Physiol, vol. 285, pp. H2194-H2200, 2003.

De Bruyne et al., "Simultaneous Coronary Pressure and Flow Velocity Measurements in Humans," Circulation, vol. 94, pp. 1842-1849, 1996.

H. Vernon Anderson et al., "Coronary Atery Flow Velocity is Related to Lumen Area and Regional Left Ventricular Mass," Circulation, vol. 102, pp. 48-54, 2000.

Itu, Lucian et al., "A Parameter Estimation Framework for Patient-Specific Hemodynamic Computations," Journal of Computational Physics, pp. 316-333, Oct. 22, 2014.

Itu et al., "A Machine-Learning Approach for Computation of Fractional Flow Reserve from Coronary Computed Tomography"; J Appl Physiol; Apr. 14, 2016; vol. 121; pp. 42-52.

Koo, Bon-Kwon, et al., "Diagnosis of Ischemia-Causing Coronary Stenoses by Noninvasive Fractional Flow Reserve Computed from Coronary Computed Tomographic Angiograms," Journal of the AmericanCollege of Cardiology, vol. 58, No. 19, 2011, pp. 1989-1997.

Renker, Matthias, et al., "Comparison of Diagnostic Value of a Novel Noninvasive Coronary Computed Tomography Angiography Method Versus Standard Coronary Angiography for Assessing Fractional Flow Reserve," Nov. 1, 2014, vol. 114, Issue 9, pp. 1303-1308.

Coenen, Adriaan, et al., "Fractional Flow Reserve Computed from Noninvasive CT Angiography Data: Diagnostic Performance of an

(56) References Cited

OTHER PUBLICATIONS

On-Site Clinician-Operated Computational Fluid Dynamics Algorithm," Radiology, vol. 274, No. 3, Mar. 2015, pp. 674-683.

Yang, Dong Hyun, et al., "Diagnostic Performancy of On-Site CT-Derived Fractional Flow Reserve Versus CT Perfusion," European Heart Journal, Cardiovascular Imaging, vol. 18, Issue 4, Apr. 1, 2017, pp. 432-440.

Morris, Paul D., et al., Virtual Fractional Flow Reserve From Coronary Angiography: Modeling the Significance of Coronary Lesions, JACC: Cardiovascular Interventions, The American College of Cardiology Foundation, vol. 6, No. 2, 2013, pp. 149-157.

Tu, Shengxian, et al., "Fractional Flow Reserve Calculation From 3-Dimensional Quantitative Coronary Angiography and TIMI Frame Count," ACC: Cardiovascular Interventions, The American College of Cardiology Foundation, vol. 7, No. 7, 2014, pp. 768-777.

Papafaklis, Michail I., et al., "Fast Virtual Functional Assessment of Intermediate Coronary Lesions Using Routine Angiographic Data and Blood Flow Simulation in Humans: Comparison with Pressure Wire-Fractional Flow Reserve," EuroIntervention: Journal of EuroPCR in Collaboration with the Working Group on Interventional Cardiology of the European Society of Cardiology, Sep. 1, 2014, vol. 10, No. 5; pp. 574-583.

Troebs, Monique, et al., "Comparison of Fractional Flow Reserve Based on Computational Fluid Dynamics Modeling Using Coronary Angiographic Vessel Morphology Versus Invasively Measured Fractional Flow Reserve," The American Journal of Cardiology, vol. 117, Issue 1, Jan. 1, 2016; pp. 29-35.

International Search Report dated Oct. 29, 2019 in corresponding International Patent Application No. PCT/EP2018/070254.

Castrounis; "Artificial Intelligence, Deep Learning, and Neural Networks Explained"; Sep. 1, 2016, Retrieved from the Internet; URL:https://www.innoarchitech.com/artificial-intelligence-deep-learning-neural-networks-explained/[retrieved on Aug. 16, 2018] the whole document.

Zreik, et al: "Automatic Detection and Characterization of Coronary Artery Plaque and Stenosis using a Recurrent Convolutional Neural Network in Coronary CT Angiography"; Apr. 12, 2018; arxiv.org, Cornell University Library; 201 Olin Library Cornell University Ithaca; NY 14853.

\* cited by examiner

NON-INVASIVE ASSESSMENT AND THERAPY GUIDANCE FOR CORONARY ARTERY DISEASE IN DIFFUSE AND TANDEM LESIONS

This application claims the benefit of U.S. Provisional Application No. 62/539,575, filed Aug. 1, 2017 and European Patent Application No. 17465533.2 filed Aug. 1, 2017, the disclosures of which are herein incorporated by reference in their entirety.

BACKGROUND OF THE INVENTION

The present invention relates to non-invasive assessment and therapy planning for coronary artery disease from medical images, and more particularly to non-invasive assessment of the hemodynamic significance of diffuse and/or tandem lesions in coronary arteries and guidance for optimal treatment of such coronary artery lesions.

Cardiovascular disease (CVD) is the leading cause of deaths worldwide. Among various CVDs, coronary artery disease (CAD) accounts for nearly fifty percent of those deaths. CAD is typically caused by lesions, such as local narrowing, or stenosis, in the coronary arteries. One treatment option for treating CAD is Percutaneous Coronary Intervention (PCI), which is a procedure that uses a catheter to place a metal or polymer stent in the coronary artery to open up the lumen. However, optimal treatment of diffuse and tandem lesions is difficult. Diffuse coronary artery lesions are lesions that reduce hemodynamic function of a whole coronary artery branch, but are not small localized stenoses. Tandem coronary artery lesions are two (or more) stenoses that are close together in series in a coronary artery branch. While full lesion coverage is generally recommended for diffuse or tandem lesions to reduce the occurrence of restenosis, longer stent length has been associated with adverse clinical outcomes through stent thrombosis and restenosis. "Spot" implantation of drug eluting stents has show promising results yielding favorable short-term and long-term clinical applications for long coronary artery lesions. However, stent gaps or incomplete lesion coverage could correlate with increased risk of future cardiovascular events.

Fractional flow reserve (FFR) is typically used to measure the hemodynamic significance of coronary artery stenoses. FFR is typically measured invasively by inserting a pressure wire into the stenosed vessel while using adenosine to induce a hyperemic state in the patient. FFR pullback curve analysis is a useful tool for stenosis severity assessment and intervention planning in complex scenarios including diffuse and tandem lesions. FFR pullback measures pressure/FFR variation along a vessel by acquiring pressure measurements with a pressure wire while pulling the pressure wire back through the vessel. By analyzing pressure variation along the vessel, a physician can identify the most sever flow limiting lesions and formulate a treatment plant. However, FFR pullback is challenging in that it requires a longer procedure with prolonged infusion of adenosine which can cause significant chest discomfort and dyspnea in the patient. These challenges have partial motivated the success of alternative indices that do not require hyperemic agents, such as instantaneous wave-free ratio (iFR), which has demonstrated good predictive power (via iFR pullback curve analysis) for the identification of significant stenoses in tandem/diffusely diseased vessels.

With or without the use of hyperemic agents, pullback curve analysis is still time consuming and invasive. It requires a first distal measurement for evaluations of significant coronary artery disease, then a controlled pull-back for identification of stenoses and assessment of the relative severity of the detected stenoses. PCI of the most severe stenosis is then performed followed by a distal measurement for evaluation of residual ischemia. If significant ischemia is indicated, the procedure is repeated until all significant lesions in the vessels have been identified and treated. The prolonged procedure time elevates the risks for the patients, as well as the cost. Furthermore, pullback curve analysis by itself does not provide an indication of risk of short-term or long-term clinical outcomes, since it ignores other effects determining vulnerability of the coronary lesion.

There is a need for fast and non-invasive techniques to assess the hemodynamic significance of different portions of long diffuse/tandem lesions, as well as guide the optimal treatment strategy based on characterization of the lesion stability before and after PCI.

BRIEF SUMMARY OF THE INVENTION

The present invention provides a method and system for computer-based non-invasive assessment and therapy guidance for coronary artery disease (CAD) from medical images. Embodiments of the present invention provide improved accuracy for non-invasive estimation of hemodynamic indices, such as fractional flow reserve (FFR), in dense and tandem coronary artery lesions.

In an embodiment of the present invention, a method for non-invasive assessment and therapy planning for coronary artery disease from medical image data of a patient comprises: extracting geometric features from medical image data representing at least a portion of a coronary artery tree of the patient; detecting one or more lesions in coronary artery tree of the patient and computing a hemodynamic quantity of interest at a plurality of points along the coronary artery tree including multiple points within each of the one or more lesions based on the extracted geometric features using a first machine learning model, resulting in an estimated pullback curve for the hemodynamic quantity of interest; predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options; and displaying a visualization of a treatment prediction for at least one of the candidate treatment options for the patient.

In an embodiment, the first machine learning model comprises a first trained regression model and a second trained regression model, and detecting one or more lesions in coronary artery tree of the patient and computing a hemodynamic quantity of interest at a plurality of points along the coronary artery tree including multiple points within each of the one or more lesions based on the extracted geometric features using a first machine learning algorithm, resulting in an estimated pullback curve for the hemodynamic quantity of interest, comprises: computing the hemodynamic quantity of interest at points along healthy segments of the coronary artery tree using the first trained regression model; and computing the hemodynamic quantity of interest at the multiple points within each of the one or more lesions using the second trained regression model.

In an embodiment, computing the hemodynamic quantity of interest at the multiple points within each of the one or more lesions using the second trained regression model comprises, for each of the one or more lesions: computing a total pressure drop feature for the lesion based on values of hemodynamic quantity of interest proximal and distal to lesion computed by the first trained regression model; inputting the total pressure drop feature, features characterizing the entire lesion, and features characterizing the multiple points within the lesion to the second trained regression model; and computing the hemodynamic quantity of interest at the multiple points within the lesion based on the total pressure drop feature, the features characterizing the entire lesion, and the features characterizing the multiple points within the lesion to the second trained regression model using the second trained regression model.

In an embodiment, the first trained machine learning model comprises a trained recurrent neural network (RNN), and detecting one or more lesions in coronary artery tree of the patient and computing a hemodynamic quantity of interest at a plurality of points along the coronary artery tree including multiple points within each of the one or more lesions based on the extracted geometric features using a first machine learning algorithm, resulting in an estimated pullback curve for the hemodynamic quantity of interest, comprises: sequentially inputting local features for each of a plurality of centerline points along a centerline of the coronary artery tree to the trained RNN; and for each of the plurality of centerline points along the centerline of the coronary artery tree, computing the hemodynamic quantity of interest at that centerline point using the trained RNN by updating an internal state of the RNN based on the local features input for that centerline point and computing the hemodynamic quantity of interest at that centerline point based on the updated internal state of the RNN.

In an embodiment, the first machine learning model comprises a trained convolutional neural network (CNN), and detecting one or more lesions in coronary artery tree of the patient and computing a hemodynamic quantity of interest at a plurality of points along the coronary artery tree including multiple points within each of the one or more lesions based on the extracted geometric features using a first machine learning algorithm, resulting in an estimated pullback curve for the hemodynamic quantity of interest, comprises: for each of one or more branches of the coronary artery tree, inputting one or more local geometric features extracted at each of a plurality of equal spaced locations along the branch to the trained CNN as an M×N array, where N is a number of the equally spaced locations and M is a number of local geometric features input for each of the equally spaced locations, and computing the hemodynamic quantity of interest at each of a plurality of equally spaced locations along the branch based on the input array of local features using the trained CNN.

In an embodiment, the CNN inputs a radius value at each of the plurality of equally spaced locations and outputs a pressure value at each of the plurality of equally spaced locations.

In an embodiment, each of the one or more candidate treatment options corresponds to a candidate percutaneous coronary intervention (PCI) treatment, and predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options, comprises: inputting the extracted geometric features to a second trained machine learning model; predicting patient-specific post-PCI geometric features for each of the one or more candidate PCI treatments based on the input geometric features using the second trained machine learning model; and predicting, for each of the one or more candidate PCI treatments, post-PCI values for the hemodynamic quantity of interest at the plurality of points along the coronary artery tree including the multiple points within each of the one or more lesions based on the predicted patient-specific post-PCI geometric features using the first machine learning model.

In an embodiment, each of the one or more candidate treatment options corresponds to a candidate percutaneous coronary intervention (PCI) treatment, and predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options, comprises: inputting the extracted geometric features, a number of the lesions detected in the coronary artery tree of the patient, and locations of the lesions detected in the coronary artery tree of the patient to a second trained machine learning model; and predicting, for each of one or more candidate PCI treatments corresponding to respective possible combinations of stenting at the detected lesions in the coronary artery tree, post-PCI values for the hemodynamic quantity of interest at the plurality of points along the coronary artery tree including the multiple points within each of the one or more lesions based on the input extracted geometric features using the second trained machine learning model.

In an embodiment, each of the one or more candidate treatment options corresponds to a candidate percutaneous coronary intervention (PCI) treatment, and the method further comprises: predicting, for each of the one or more candidate PCI treatments, a plaque vulnerability index using a second trained machine learning model based on the geometric features corresponding to post-PCI anatomy for each of the one or more candidate PCI treatments and other features including one or more of demographic features or blood biomarkers.

In an embodiment, predicting, for each of the one or more candidate PCI treatments, a plaque vulnerability index using a second trained machine learning model based on the geometric features corresponding to post-PCI anatomy for each of the one or more candidate PCI treatments and other features including one or more of demographic features or blood biomarkers comprises: predicting, for each of the one or more candidate PCI treatments, the plaque vulnerability index at the plurality of points along the coronary artery tree including the multiple points within each of the one or more lesions using the second trained machine learning model, resulting in a respective predicted plaque vulnerability curve for each of the one or more candidate PCI treatments, wherein the plaque vulnerability index at each point corresponds to a likelihood that the vascular location will cause a cardiovascular event.

In an embodiment, each of the one or more candidate PCI treatments includes one or more stenting locations, and displaying a visualization of a treatment prediction for at least one of the candidate treatment options for the patient comprises: displaying, for at least one of the candidate PCI treatments, an image showing at least a portion of the coronary artery tree of the patient with a visual representation of a stent overlaid on the coronary artery at the one or more stenting locations for the candidate PCI treatment, the predicted plaque vulnerability index curve for the candidate PCI treatment, and the predicted post-treatment pullback curve for the hemodynamic quantity of interest for the candidate PCI treatment.

In an embodiment, the method further comprises: scoring the one or more candidate PCI treatments based on the predicted post-treatment values of the hemodynamic quantity of interest and the predicted plaque vulnerability index for each of the one or more candidate PCI treatments.

In an embodiment, scoring the one or more candidate PCI treatments based on the predicted post-treatment values of the hemodynamic quantity of interest and the predicted plaque vulnerability index for each of the one or more candidate PCI treatments comprises: automatically excluding all candidate PCI treatments for which the predicted post-treatment values of the hemodynamic quantity of interest fall below a threshold value; and assigned a score to each of the remaining candidate PCI treatments based on the integral average of the predicted plaque vulnerability index.

In an embodiment, the one or more candidate PCI treatments include multiple stenting scenarios for stenting at least one of the lesions, including spot stenting at one or more locations within the lesion and complete stenting of the lesion.

In an embodiment, the method further comprises: generating post-PCI scenarios corresponding to each of the one or more candidate PCI treatments using a third trained machine learning model, wherein the third trained machine learning model is trained in a generative adversarial network (GAN).

In an embodiment, the method further comprises: prior to detecting the one or more lesions in coronary artery tree and computing the hemodynamic quantity of interest at the plurality of points along the coronary artery tree including the multiple points within each of the one or more lesions based on the extracted geometric features using a first machine learning model, identifying a mismatch between an anatomical and functional evaluation in at least one branch of the coronary artery tree and modifying the extracted geometric features in the at least one branch of the coronary artery tree to correct the mismatch between the anatomical and functional evaluation.

In an embodiment of the present invention, an apparatus for non-invasive assessment and therapy planning for coronary artery disease from medical image data of a patient comprises: means for extracting geometric features from medical image data representing at least a portion of a coronary artery tree of the patient; means for detecting one or more lesions in coronary artery tree of the patient and computing a hemodynamic quantity of interest at a plurality of points along the coronary artery tree including multiple points within each of the one or more lesions based on the extracted geometric features using a first machine learning model, resulting in an estimated pullback curve for the hemodynamic quantity of interest; means for predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options; and means for displaying a visualization of a treatment prediction for at least one of the candidate treatment options for the patient.

In an embodiment of the present invention, a non-transitory computer readable medium stores computer program instructions for non-invasive assessment and therapy planning for coronary artery disease from medical image data of a patient. The computer program instructions, when executed by a processor, cause the processor to perform operations comprising: extracting geometric features from medical image data representing at least a portion of a coronary artery tree of the patient; detecting one or more lesions in coronary artery tree of the patient and computing a hemodynamic quantity of interest at a plurality of points along the coronary artery tree including multiple points within each of the one or more lesions based on the extracted geometric features using a first machine learning model, resulting in an estimated pullback curve for the hemodynamic quantity of interest; predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options; and displaying a visualization of a treatment prediction for at least one of the candidate treatment options for the patient.

These and other advantages of the invention will be apparent to those of ordinary skill in the art by reference to the following detailed description and the accompanying drawings.

DETAILED DESCRIPTION

Figure 1:
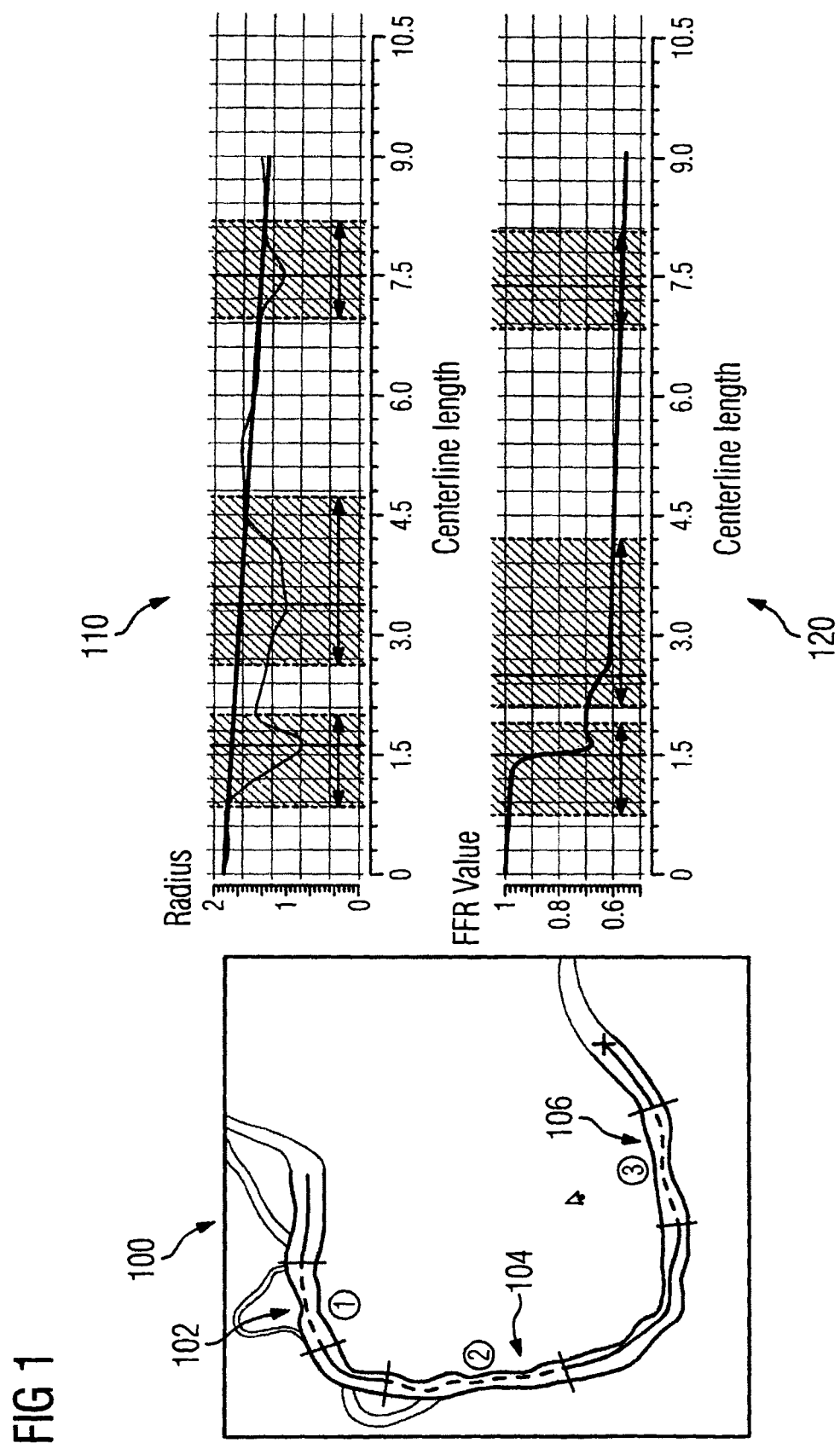
FIG. 1 illustrates an example of lesion and scoring in a medical image of a patient.

The present invention relates to computer-based non-invasive assessment and therapy guidance for computer-based non-invasive assessment and therapy guidance for coronary artery disease (CAD) from medical images. Embodiments of the present invention provide improved accuracy for non-invasive estimation of hemodynamic indices, such as fractional flow reserve (FFR), in dense and tandem coronary artery lesions. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or a remote computer system.

Various techniques have been proposed to non-invasively approximate FFR and the FFR pullback curve using computational modeling (i.e., computational fluid dynamics simulations). The main challenges associated with the use of "virtual FFR" as a surrogate for invasively measured FFR (especially for PCI guidance in the cathlab) are accuracy, real-time performance, and ease of use. Existing computer-based techniques for determining virtual FFR using computational modeling require several steps: segmentation of the vascular structure of interest; definition of boundary conditions constraining the blood flow simulation problem; and a numerical solution of the blood flow simulation problem equations (e.g., 3D Navier-Stokes equations). Each of these steps relies on assumptions, potentially introducing errors and loss of accuracy. Furthermore, the steps for determining virtual FFR using computational modeling require a large computational effort and processing time.

Embodiments of the present invention use machine learning methods to estimate virtual FFR. The use of such machine learning methods provides an advantage of increasing processing speed as compared with existing computational methods, since the computational cost is moved almost entirely to an off-line training phase. This enables real-time evaluation of virtual FFR. In addition, the machine learning methods described herein are intrinsically data-driven, in the sense that segmentation of the patient-specific anatomy or modeling of boundary conditions is not required as long as input feature for the machine learning model can be directly determined from the medical image scan data. Another advantage of the machine learning methods for estimating virtual FFR is that they can be fully automated because they can be posed as an additional image reading step. Further, the machine learning methods can be applied to estimation of other quantities in addition to FFR, such as instantaneous wave-free ratio (iFR), rest Pd/Pa, or further hemodynamic quantities.

Existing techniques for computer-based determination of virtual FFR use computational modeling to simulate blood pressure in coronary artery stenoses. However, the behavior of blood pressure and FFR values in diffuse and tandem lesions can be much different as compared to other stenoses, and existing techniques are often inaccurate in diffuse and tandem lesions. Embodiments of the present invention provide machine learning methods that improve the accuracy of the estimated FFR values in diffuse and tandem lesions, as compared to existing techniques. For example, an embodiment described herein utilizes cascaded trained surrogate models (FIG. 4) to compute the virtual FFR values (or other hemodynamic indices). Another embodiment described herein utilizes a trained recurrent neural network (RNN) (FIG. 5) to compute the virtual FFR values (or other hemodynamic indices). Another embodiment described herein utilizes a convolutional neural network (CNN) (FIG. 6) to compute the virtual FFR values (or other hemodynamic indices). Each of these embodiments provides increased accuracy as compared with existing computer-based techniques for estimating virtual FFR.

In an advantageous embodiment of the present invention, the above described analysis for computer virtual FFR can be combined with other information to provide a holistic assessment of plaque vulnerability. Embodiments of the present invention provide automatic detection of plaque in coronary vessel anatomies purely based on imaging features, as well as machine-learning powered methods for the assessment of plaque vulnerability based on imaging data as well as other patient-specific medical data.

Medical imaging technologies, such as intravascular ultrasound (IVUS), optical coherence tomography (OCT), near-infrared spectroscopy, etc., allow clear visualization of the plaque in a vessel and analysis of its structure. This allows for a classification of the plaque and correlation with long term outcomes. Note that plaque vulnerability is currently defined as a plaque with specific morphology features, usually referring exclusively to thin cap fibroatheromas (or positive remodeling, spotty calcification, or large necrotic core). That is, the plaque vulnerability is based solely on intrinsic factors. However, the present inventors have recognized that it would be advantageous for a vulnerable plaque to be defined as a plaque that is prone to rupture/erosion when all intrinsic and extrinsic effects (dynamic pressure/pressure head, turbulent/laminar flow, shear stress, rheological properties, systematic conditions) are taken into account, regardless of plaque structure. Hence, embodiments of the present invention provide a comprehensive plaque vulnerability analysis the combines anatomical, hemodynamic, and systemic markers to provide a holistic and accurate plaque assessment. Such plaque vulnerability analysis may provide as output a treatment indication, for example for a systemic approach (e.g., medical treatment) and/or a localized approach (e.g., plaque sealing through angioplasty). No solution has previously been proposed for an integrated decision support system for the management of long and diffuse stenoses, combining the identification of target lesions as well as guidance for optimal therapy based on assessment of pre- and post-PCI plaque stability.

Detection of lesions can be performed using a regressor trained with a recurrent neural network to estimate the stenosis severity based on the vessel radius. The estimated stenosis severity can be used to define a score for the different lesions or portions of the lesions, with a higher score being associated with higher regressed stenosis severity. The different lesions (or portions of lesions) can then be ordered and labeled progressively with decreasing severity score. FIG. 1 illustrates an example of lesion and scoring in a medical image of a patient. As shown in FIG. 1, image 100 shows a medical image of a coronary artery, in which three stenoses 102, 104, and 106 have been identified. Image 110 shows the radius of the coronary artery lumen along the centerline length of the coronary artery. The severity of the stenoses 102, 104, and 106 can be scored based on the coronary artery radius. The stenoses 102, 104, and 106 are labeled progressively with decreasing severity score as stenoses 1, 2, and 3, respectively.

In another embodiment, the identification and scoring of the lesions can be performed by computing virtual FFR (vFFR) along the length of the vessel. For example, a machine learning based method for computing vFFR can be used, such as the method described in U.S. Pat. No. 9,349, 178, which is incorporated herein by reference in its entirety. Additional machine learning based methods for computing vFFR are described herein as well. Based on a segmentation of an anatomical model of the coronary tree visualized in the medical images of the patient, a set of geometric features can be extracted and provided as input to a regressor trained with a machine learning algorithm. The trained regression model estimates vFFR for each location in the anatomical model. The most hemodynamically significant lesions can be defined as the one that causes the largest variation of vFFR (or virtual iFR) across the lesion. As shown in FIG. 1, image 120 shows the vFFR computed along the centerline length of the coronary artery. The computed vFFR can be used to score the severity of the stenoses 102, 104, and 106.

Figure 2:
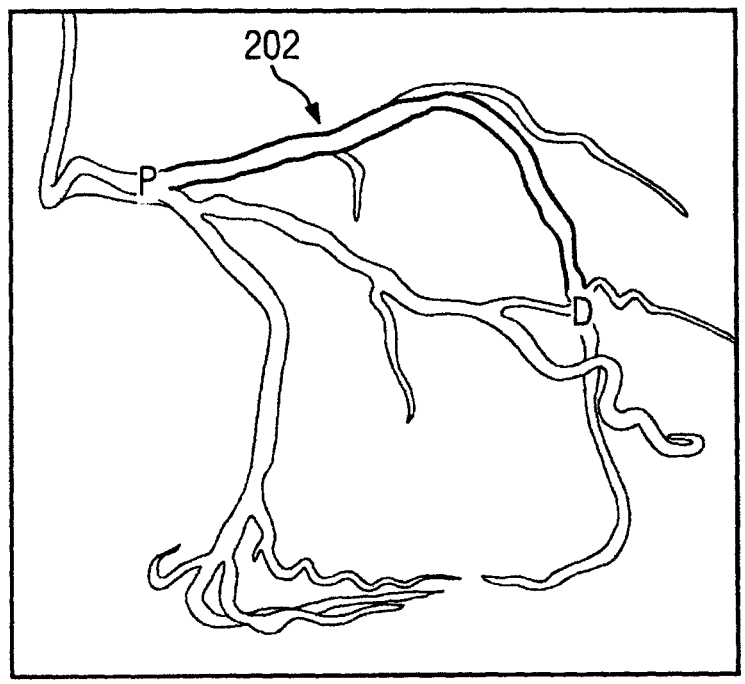
FIG. 2 illustrates an example of a left anterior descending (LAD) artery with diffuse coronary artery disease visualized under post-PCI conditions, with a mismatch between the anatomical assessment and the functional assessment.

In cases of diffuse coronary artery disease which affects an entire vessel, i.e., no specific stenosis can be identified, a mismatch between the anatomical and functional assessment of the coronary artery is typically the result. This means that from an anatomical point of view the artery appears to be normal, but when evaluated with a functional diagnostic index, e.g., FFR, significant coronary artery disease may be diagnosed. Since image-based methods rely mainly on the medical images of the coronary arteries, cases of diffuse coronary artery disease are particularly hard to diagnose correctly without performing invasive measurements. This is true for both pre-PCI and post-PCI computations. FIG. 2 illustrates an example of a left anterior descending (LAD) artery 202 with diffuse coronary artery disease visualized under post-PCI conditions, with a mismatch between the anatomical assessment (% DS<30%) and the functional assessment (invasive FFR=0.71). Without taking into account further information related to diffuse coronary artery disease, it is very difficult to correctly non-invasively diagnose this artery.

Figure 3:
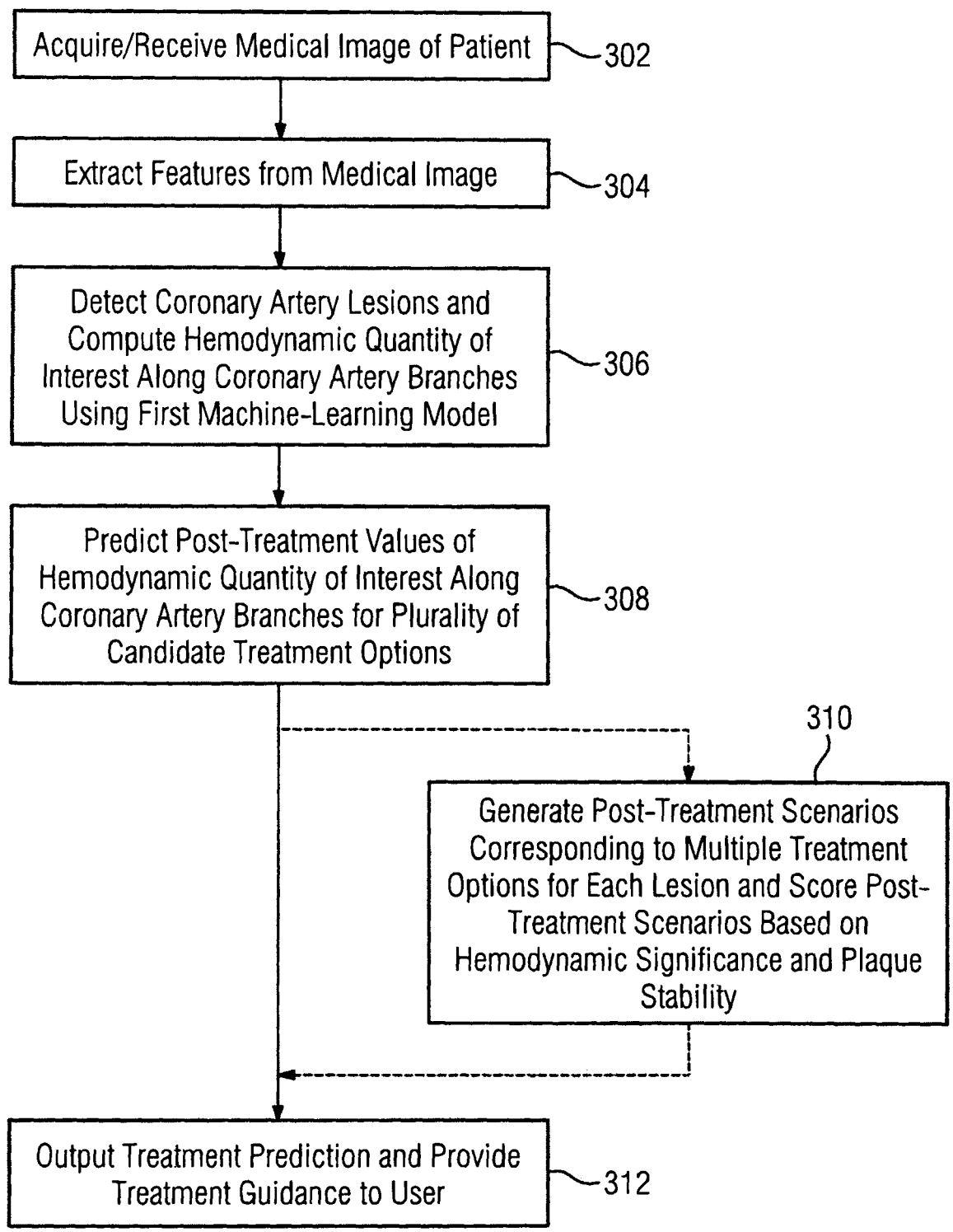
FIG. 3 illustrates a method of non-invasive assessment and therapy planning for coronary artery disease (CAD) according to an embodiment of the present invention.

FIG. 3 illustrates a method of non-invasive assessment and therapy planning for coronary artery disease (CAD) according to an embodiment of the present invention. The method of FIG. 3 provides improved results diagnosis and treatment planning for diffuse lesions, tandem lesions, and multiple lesions, as compared with previous techniques. The method of FIG. 3 utilizes a combination of image analytics and computational modeling to assess the risk associated with coronary lesions before and after intervention. The method of FIG. 3 computes an accurate FFR distribution (pullback) along an analyzed coronary artery segment. The method of FIG. 3 allows the online computation of FFR, as well as other hemodynamic quantities of interest (e.g., iFR). As the embodiments described herein for computing the virtual pullback FFR curve are very fast, various options can be derived for individual stenosis assessment and/or treatment planning/prediction in multiple or diffused stenosis settings.

Referring to FIG. 3, at step 302, one or more medical images of the coronary arteries of the patient are acquired/ received. Medical image data from one or multiple imaging modalities can be acquired. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D, or 4D (3D+time) medical image data. The medical image data can be received by a computer/ processor directly from one or more image acquisition devices used to acquire the medical images, such as a CT scanner, X-ray scanner, MR scanner, Angiography scanner, Ultrasound device, etc., or the medical image data may be received by loading previously stored medical image data for a patient. The computer/processor and image acquisition device (e.g., CT scanner) can be implemented in the same device or can be implemented in separate devices. In an advantageous embodiment, the medical images are 3D coronary CT angiography (CTA) images acquired in a 3D coronary CTA scan using a CT scanner. Coronary CTA images ensure that the coronary vasculature is adequately imaged using a contrast agent that is injected into the patient. In another possible embodiment, X-ray angiography images can be acquired.

At step 304, features are extracted from the medical images of the coronary arteries of the patient. The features include geometrical features representing the geometry of the coronary artery branches in the medical images. The features may be extracted for the entire coronary artery tree or for a particular target portion (i.e., target branch or branches) of the coronary artery tree. The features can include features characterizing the geometry and morphology of the stenoses, feature characterizing the geometry of each coronary artery branch, and features characterizing the entire coronary artery tree. The specific features extracted may depend on the machine-learning based method used to perform the computation of the hemodynamic quantity of interest (e.g., FFR) in step 306, and the features extracted for the various machine-learning methods described herein are discussed in greater detail below.

In one embodiment, the features can be extracted by first generating a patient-specific anatomical model of the coronary arteries from the medical image data and then extracting the geometric features from the patient-specific anatomical model. In this case, the patient-specific anatomical model can be generated by segmenting the coronary arteries in the medical image data using an automated coronary artery centerline extraction algorithm. For example, the coronary arteries can be segmented in a CT volume using the method described United States Published Patent Application No. 2010/0067760, entitled "Method and System for Automatic Coronary Artery Detection," the disclosure of which is incorporated herein by reference in its entirety. Once a coronary artery centerline tree is extracted, cross-section contours can be generated at each point of the centerline tree. The cross-section contour at each centerline point gives a corresponding cross-section area measurement at that point in the coronary artery. In one exemplary implementation, the features can be extracted from the extracted centerlines and cross-section contours. In another exemplary implementation, a 3D mesh can be generated from the centerlines and cross-section contours and the features can be extracted from the 3D mesh. In this case, a 3D anatomical surface model is generated for the segmented coronary arteries. For example, methods for anatomical modeling of the coronary arteries are described in U.S. Pat. No. 7,860, 290, entitled "Three-Dimensional (3D) Modeling of Coronary Arteries," and U.S. Pat. No. 7,953,266, entitled "Robust Vessel Tree Modeling," the disclosures of which are incorporated herein by reference in their entirety. In another embodiment, the features can be extracted directly from the medical image data without first generating an anatomical model. In this case, the features can be purely image-based (e.g., based on image intensity).

At step 306, coronary artery lesions are detected and a hemodynamic quantity of interest is computed along one or more branches of the coronary artery tree using a first machine-learning algorithm. The computation of the hemodynamic quantity of interest along the one or more branches of the coronary artery tree results in generation of a virtual pullback curve for the hemodynamic quantity of interest. In an advantageous embodiment of the present invention, the hemodynamic quantity of interest is FFR. As the FFR values are computed non-invasively based on the medical image data of the patient using computer-based computations, the computed FFR is referred to herein as "virtual FFR" (vFFR). In other embodiments, other hemodynamic quantities of interest can be computed non-invasively, such as iFR, rest distal-to-aortic pressure ratio (Pd/Pa), computational flow reserve (CFR), hyperemic stenosis resistance (HSR), baseline stenosis resistance (BSR), index of microvascular resistance (IMR), or wall shear stress. Depending on the machine-learning algorithm used for this step, the detection of the lesions/stenoses and the computation of the hemodynamic quantity of interest may be performed together by the same machine-learning model or may be performed separately using different machine learning models. Three machine-learning algorithms for are described herein for computation of the hemodynamic quantity of interest/detection of the coronary artery lesions. Each of the machine-learning algorithms described herein improves the accuracy of the computation of FFR (or other hemodynamic quantities) in diffuse and tandem lesions. Although these embodiments are described herein as computing FFR, it is to be understood that these embodiments may be similarly applied to compute other hemodynamic quantities, as well.

In a first embodiment, the virtual pullback curve is computed using cascaded trained vFFR regression models. Blood flow conditions are significantly altered in stenosis regions (lesions) due to a number of reasons, including sharp radius variations, irregular/non-circular cross-sectional lumen shape, formations of jets after narrow stenoses, etc. Accordingly, computation of vFFR is very sensitive to the geometry features in the stenosis region and it is important that the accuracy of a machine-learning regression model be specifically controlled in the stenosis region. With the goal of improving accuracy of a vFFR regression model in the stenosis region, a trained vFFR regression model, such as the regression model trained using the method described in U.S. Pat. No. 9,349,178, can be augmented with additional machine-learning trained vFFR model applied in a cascaded fashion. In particular, once a first vFFR regressor predicts the total pressure drop along the stenosis, this value is used as a feature of a second vFFR regressor that predicts the variation of the pressure inside the stenosis. In this embodiment, lesions (stenosis regions) are detected (e.g., using a separate machine-learning based model) prior to computing the vFFR pullback curve using the cascaded trained vFFR regressors. For example, detection of lesions can be performed using a regressor trained with a recurrent neural network to estimate stenosis locations based on the vessel radius.

Figure 4:
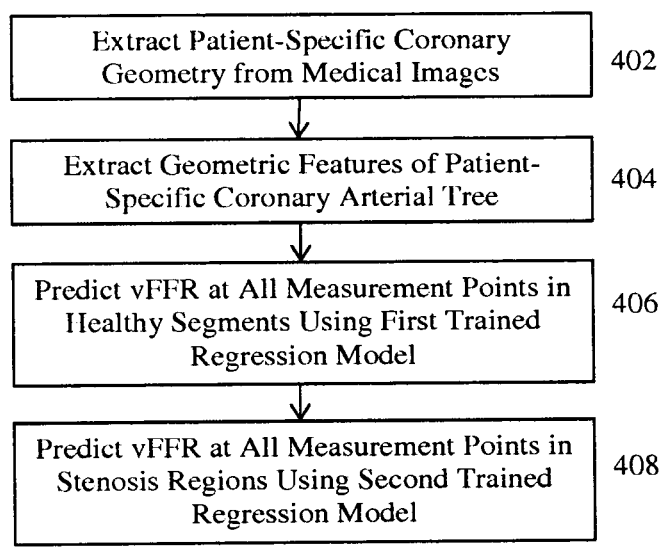
FIG. 4 illustrates a method for predicting virtual FFR (vFFR) in coronary arteries of a patient using cascaded machine-learning models according to an embodiment of the present invention.

FIG. 4 illustrates a method for predicting vFFR in coronary arteries of a patient using cascaded machine-learning models according to an embodiment of the present invention. Although not shown in FIG. 4, the method of FIG. 4 assumes that stenosis regions/lesions in the coronary artery tree have been identified. For example, stenosis regions can be automatically identified using a regressor trained with a recurrent neural network to estimate stenosis locations based on the vessel radius. As shown in FIG. 4, at step 402, patient-specific coronary geometry is extracted from the medical images (e.g., X-ray angiography, coronary CTA, etc.) of the patient. In an advantageous implementation, a patient-specific anatomical model can be generated by segmenting the coronary arteries in the medical image data using an automated coronary artery centerline extraction algorithm. Once a coronary artery centerline tree is extracted, cross-section contours can be generated at each point of the centerline tree. In a possible implementation, a 3D mesh can also be generated from the centerlines and cross-section contours and the features can be extracted from the 3D mesh.

At step 404, geometric features of the patient-specific coronary arterial tree are extracted. According to an exemplary implementation, the geometric features extracted from medical image data can include parameters characterizing the geometry of each stenosis region, such as reference diameters of the vessel proximal and distal to the stenosis, minimal lumen diameter (MLD) within the stenosis, lesion length (LL), entrance angle of the stenosis, entrance length, exit angle of the stenosis, exit length, percentage of the diameter blocked by the stenosis, and the percentage of the area blocked by the stenosis. It is also possible that additional parameters characterizing the geometry of the stenosis can be extracted, as well, or various parameters can be combined to generate additional features. Features characterizing the morphology of each stenosis region may also be extracted, such as characteristics of calcification, characteristics of the plaque, characteristics of thrombus, characteristics of diffuse disease (i.e., single stenosis or diffused stenosis along artery), the presence of total or sub-total occlusion (i.e., complete blockage or partial blockage), and the presence of myocardial bridging. The parameters characterizing the morphology of the stenosis can be binary parameters indicating presence or absence or numerical values indicating a grading for a particular parameter. The geometric features can also include features characterizing the geometry of each vessel branch, such as vessel radius and areas sampled along the centerline of the branch, terminal radius and area of the vessel branch, centerline tortuosity measures, the location of the stenosis in the branch (e.g., proximal, mid, or distal in the branch), a cumulative number of vessel narrowings in the branch proximal to each stenosis region, and a cumulative number of calcifications within the branch proximal to each stenosis region. The geometric features extracted from the medical image data can also include features characterizing the entire coronary artery tree, such as an indication of left or right dominance, size of coronary territories associated with myocardial masses, terminal radius of each coronary branch, number of lesions (stenoses) in the entire coronary tree, an indication of which segments of the coronary artery tree has lesions, bifurcations (type and angulations), trifurcations (type and angulations), the number and location of stents already implanted, and the number and location of bypass grafts.

Features characterizing the cardiac anatomy and function can also be extracted, such as end-systolic volume (ESV), end-diastolic volume (EDV), ejection fraction (EF), endocardial volume, epicardial volume, myocardial volume, trabeculae and papillary muscle volume and mass, left and right ventricular volume and mass, characteristics of contrast agent attenuation (e.g., different intensity values for each voxel from different frames of a medical image sequence), and characteristics of contrast agent propagation (e.g., a number of frames to propagate contrast agent). Additional features may be extracted from functional measurements and/or demographic information for the patient associated. Such features can include systolic blood pressure, diastolic blood pressure, mean arterial pressure, heart rate at rest and/or during stress, parameters derived from an ECG trace (e.g., QRS duration, R-R interval, etc.), past history of heart disease, past history of valve dysfunction, past history of valve repair or replacement, body mass index (BMI), body surface area (BSA), weight, height, age, and sex. The features for the patient's past history may be binary, indicating that there is a past history or not, or categorical, providing further indication of a category of the past history. In an advantageous embodiment, the features include an ischemic weight and an ischemic contribution score. The ischemic weight is an ischemic weight value associated with each coronary artery segment (i.e., root, interior, or leaf segment). The ischemic contribution score is computed for specific finite length segments of coronary artery geometry comprising one or more branches. The ischemic contribution score is computed from a series of geometric properties and from ischemic weights of the particular segments. The ischemic weight and ischemic contribution score features can be computed as described in U.S. Pat. No. 9,349,178, entitled "Synthetic Data-Driven Hemodynamic Determination in Medical Imaging" and U.S. Publication No. 2017/0245821, entitled "Method and System for Purely Geometric Machine Learning Based Fractional Flow Reserve," the disclosures of which are incorporated herein in their entirety by reference. In addition to the above describe features, several other derived features may also be computed from the extracted features. Examples of features to be input to the trained machine learning models are described in greater detail U.S. Pat. No. 9,349,178, entitled "Synthetic Data-Driven Hemodynamic Determination in Medical Imaging," the disclosure of which is incorporated herein in its entirety by reference.

At step 406, vFFR is predicted at all measurement locations in healthy (non-stenosis) segments of the patient-specific anatomical model of the coronary artery tree using a first trained regression model. The first trained regression model is a surrogate model that inputs the features extracted in step 404 and estimates vFFR values at each location (e.g., centerline point) in the patient-specific anatomical model of the coronary arteries. The first trained regression model can be implemented as described in U.S. Pat. No. 9,349,178, entitled "Synthetic Data-Driven Hemodynamic Determination in Medical Imaging," the disclosure of which is incorporated herein in its entirety by reference. In an advantageous implementation, the first trained regression model can be trained as a Support Vector Regressor (SVR). The first trained regression model can be trained using synthetically generated geometries that are not based on patient-specific data. Such geometries may be generated by varying the shape, severity, location, and number of stenoses, together with the radius and locations of main and side branches in a generic model of a coronary artery vessel tree. As a simplest example of a synthetically generated geometry, one can use a straight tube with a narrowing to represent the stenosis. Multiple CFD simulations can be performed by varying the synthetic geometry (e.g., minimum radius of the stenosis, entrance angle, exit angle) and varying the inflow or outflow boundary conditions to compute the FFR value. One advantage of using synthetically generated geometries is that it does not require the collection and processing of patient-specific data for completing the training phase, thereby saving both time and cost. Further, there is no limit on the type of synthetic geometries that can be generated, thereby covering a wide spectrum of vessel shapes and topology. Using this approach, the entire training phase can be performed without any patient-specific geometry or image data. U.S. Pat. No. 9,349,178, which is incorporated herein in its entirety by reference, describes training using synthetic geometries in greater detail.

At step 408, vFFR is predicted at all measurement locations in the stenosis regions using a second trained regression model. The second trained regression model is a surrogate model that estimates vFFR values at each location (e.g., centerline point) in the stenosis regions in patient-specific anatomical model of the coronary arteries. The second trained regression model inputs features characterizing the stenosis region and locations inside the stenosis. The second trained regression model also inputs as features values computed by the first trained regression model. According to an advantageous embodiment, the features input to the second trained regression model can be divided into two groups: features characterizing the entire lesion (stenosis region) and features characterizing the locations inside the stenosis. The features characterizing the entire lesion can include reference healthy radius, proximal radius of the stenosis, distal radius of the stenosis, minimum radius of the stenosis, percentage diameter reduction at minimum radius, stenosis entrance length, stenosis minimum radius length, stenosis exit length, stenosis total length (sum of the stenosis entrance length, minimum radius length, and exit length), flow rate, and total pressure drop. The total pressure drop feature for a stenosis region is computed from the vFFR values proximal and distal to the stenosis region estimated by the first trained regression model. The features characterizing the locations inside the stenosis include the location of the cross-section with minimum radius (expressed as a distance from the start of the stenosis), relative location of the cross-section with minimum radius (expressed as percentage, where 0% corresponds to the start of the stenosis and 100% corresponds to the end of the stenosis), Boolean feature labeling the current cross-section as being placed before or after the minimum radius location, signed distance function between the current cross-section and the minimum radius location, radius at the current cross-section, and ratio between radius at the current cross-section and the minimum radius.

In an advantageous embodiment, the second trained regression model is trained using a SVR trained method. In an advantageous embodiment, the second trained regression model is trained based on synthetically generated vascular geometries and CFD simulations that provide, for each synthetic geometry, the spatial distribution of hemodynamic variables of interest (e.g., FFR or pressure drop). In the training stage, for each synthetically generated anatomy, the above described features are computed and measures of interest (e.g., FFR and/or pressure drop at each point) as computed by CFD simulations are considered as ground truth. The second trained regression model is trained to learn a mapping between the input features and the ground truth data.

When a new (unseen) vascular anatomy is presented to the system, all geometry features are extracted. The geometry features are provided as input to the first trained regression model, which estimates vFFR at all measurement locations in the healthy segments. Noting that blood pressure at each measurement point can be recovered from the estimate vFFR as Pd=Pa*(1−FFR). The "total pressure drop" feature can be computed for each stenosis region as the difference between the proximal and distal blood pressure recovered from the vFFR values estimated by the first trained regression model. This feature together with the other geometry features characterizing the entire lesion and the features characterizing the locations inside the stenosis are provided as input to the second trained regression model, which estimates vFFR at all points in each stenosis region. Combining the vFFR (and/or blood pressure) values estimated by the first and second trained regression models, vFFR (and/or blood pressure) is estimated at every location in the vascular anatomy, thus effectively generating a full virtual pullback curve.

In a second embodiment, the virtual FFR pullback curve is computed using a recurrent neural network (RNN). In this embodiment, virtual FFR (or iFR) is computed by a regression model trained with an RNN, such as a long short-term memory (LSTM) network. In this case, an analogy between a sequence of cross-sections along a centerline and a sequence of input events on a temporal line is leveraged. RNNs are designed to process a sequence of input events and they are capable of storing an internal state. The internal state is updated based on the input and determines the output, thereby allowing the network to modulate its behavior based on input events from the past. LSTM networks are a particular class of deep learning RNNs that combine the ability to recognize local features ("short-term" memory) with the context ("long-term" memory) in which they appear. In this embodiment, the RNN processes an ordered sequence of vascular cross-sections one-by-one (from the beginning to the end of the vessel), and keeps track of how the features change from past cross-sections to the current one thanks to specialized neuron layers with dedicated internal state variables. The training process teaches the network how this internal state should be updated (intuitively, how much information to keep or drop) every time a new cross-section is presented to the input channel. In this embodiment, the RNN can automatically detect the lesions (stenosis regions) in the coronary artery tree as well as computing the vFFR along the coronary artery tree.

Figure 5:
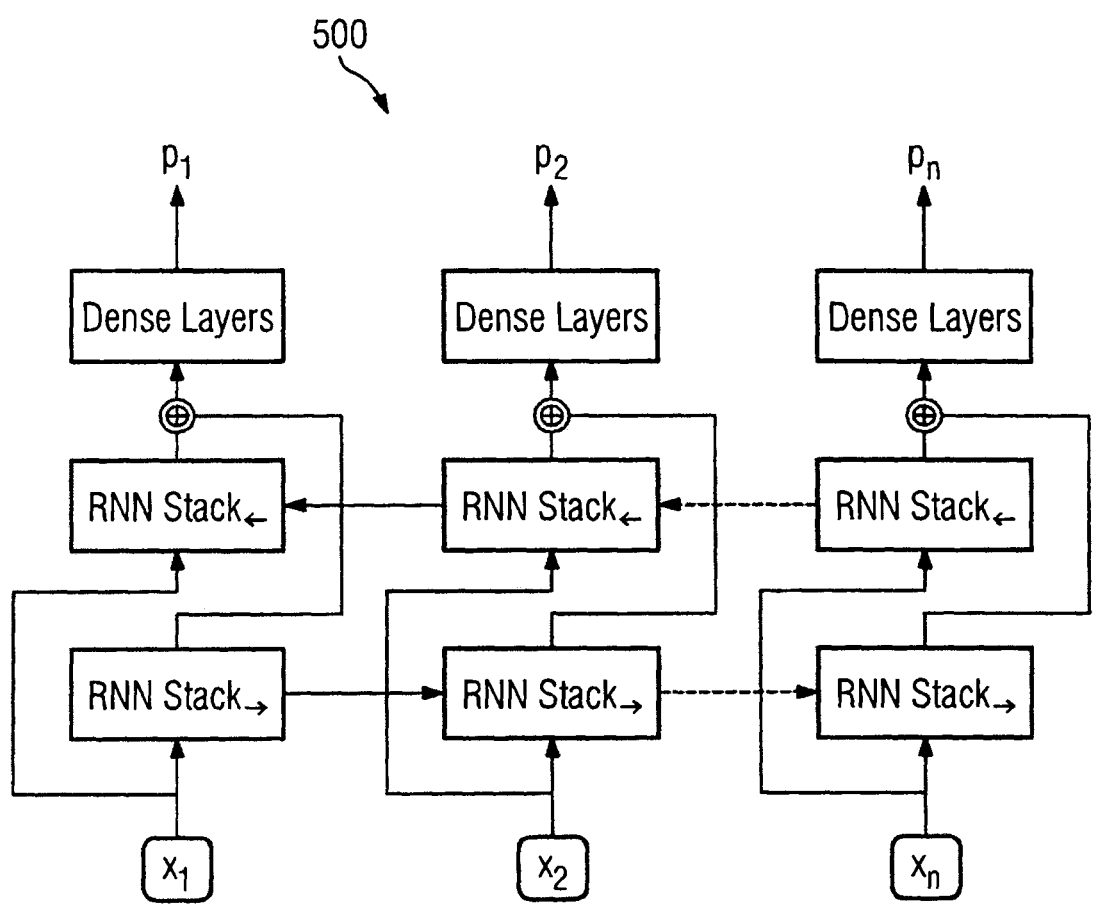
FIG. 5 illustrates an exemplary recurrent neural network (RNN) architecture for computing vFFR along the coronary anatomy of a patient according to an embodiment of the present invention.

In an advantageous implementation, the training database used to train the RNN can be made up of synthetically generated vascular geometries and CFD simulations for each geometry that provide the ground truth spatial distribution of hemodynamic variables. FIG. 5 illustrates an exemplary RNN architecture for computing vFFR along the coronary anatomy of a patient according to an embodiment of the present invention. As shown in FIG. 5, the RNN architecture 500 includes stacked bidirectional recurrent units (LSTM) with skip connections between all units in the stack. The stacked bidirectional recurrent units evaluate the centerline points along the length of a coronary artery in opposite directions (forward and backward). Each sequence element (i.e., the output vFFR value for each centerline point) is produced by concatenating the output of both stacks and passing them to multiple dense layers with ReLU activation, shrinking in size until there is only one linear output neuron in the layer. The input features $\vec{x}_i$ for each centerline point include the vessel radius at the centerline point, the spatial coordinates of the centerline point, and the blood flow rate. The output value $p_i$ is the vFFR value (or other hemodynamic quantity of interest) at the corresponding centerline point. The trained RNN provides an estimation of the quantity of interest (e.g., vFFR) along the entire length of the vascular anatomy. Since the RNN is trained to minimize the prediction error at any centerline point, a well-trained regression model will guarantee high accuracy in both healthy regions as well as in stenosis regions.

The RNN can be used to learn the effect of any geometry feature of the centerline or of the cross-section, provided the network has enough input information to derive the corresponding predictive features. For curved vessels, the full set of coordinates of each centerline point can be used to implicitly represent curvature and its variation along the centerline. For non-circular cross-sections or non-eccentric stenoses, the coordinates of the contour points of each cross section can be provided as additional input. Alternatively, derived features may be used to describe more complex anatomical settings:

Curved vessels: local curvature (1/radius);
Tandem stenoses: distance between the end location of the first stenosis and the start location of the second stenosis;
Eccentric stenoses:

$$ecc = \frac{d}{radius_{Ref} - radius_{Min}} \cdot 100$$

where d is the distance between the hypothetical centerline location of the cross-section with minimum radius and the actual centerline location of the cross-section with minimum radius (the hypothetical centerline location is computed using a spline interpolation between the start and end locations of the stenosis), $radius_{Ref}$ is the reference radius (healthy radius) of the vessels at the minimum radius location and $radius_{Min}$ is the minimum radius of the stenosis. This feature represents a relative measure of how much the centerline deviates from the supposedly healthy path of the centerline at the location of minimum radius;

Diffuse stenoses: degree of stenoses and location at radius minima locations of the diffuse lesion.

Any or all of these features can be included in the features input to the RNN for each centerline point.

In a third embodiment, the virtual FFR pullback curve is computed using a convolutional neural network (CNN). In this embodiment, a CNN can be employed to predict pressure variation or vFFR along a centerline of a coronary anatomical model of the patient. The CNN can directly predict vFFR along the centerline or predict pressure values along the centerline, in which case the vFFR values are directly computed from the predicted pressure values. In this embodiment, the CNN can automatically detect the lesions (stenosis regions) in the coronary artery tree as well as computing the pressure/vFFR along the coronary artery tree. In an advantageous implementation, a fixed number N of equally spaced locations are considered for each vessel or vessel branch. At each location, a number of features describing the local geometry of the vessel are considered. For example, at each location, geometric features such as the radius, curvature, eccentricity, stenosis degree, etc., can be input to the CNN. Thus, the input data may be represented as an M×N array, where M is the number of features at each location. The output of the CNN is represented by a K×N array, where K represents the number of independent measures of interest predicted by the network. For example, the network may be employed to not only predict pressure and/or vFFR, but also other relevant measures, like wall shear stress, velocities, etc.

Figure 6:
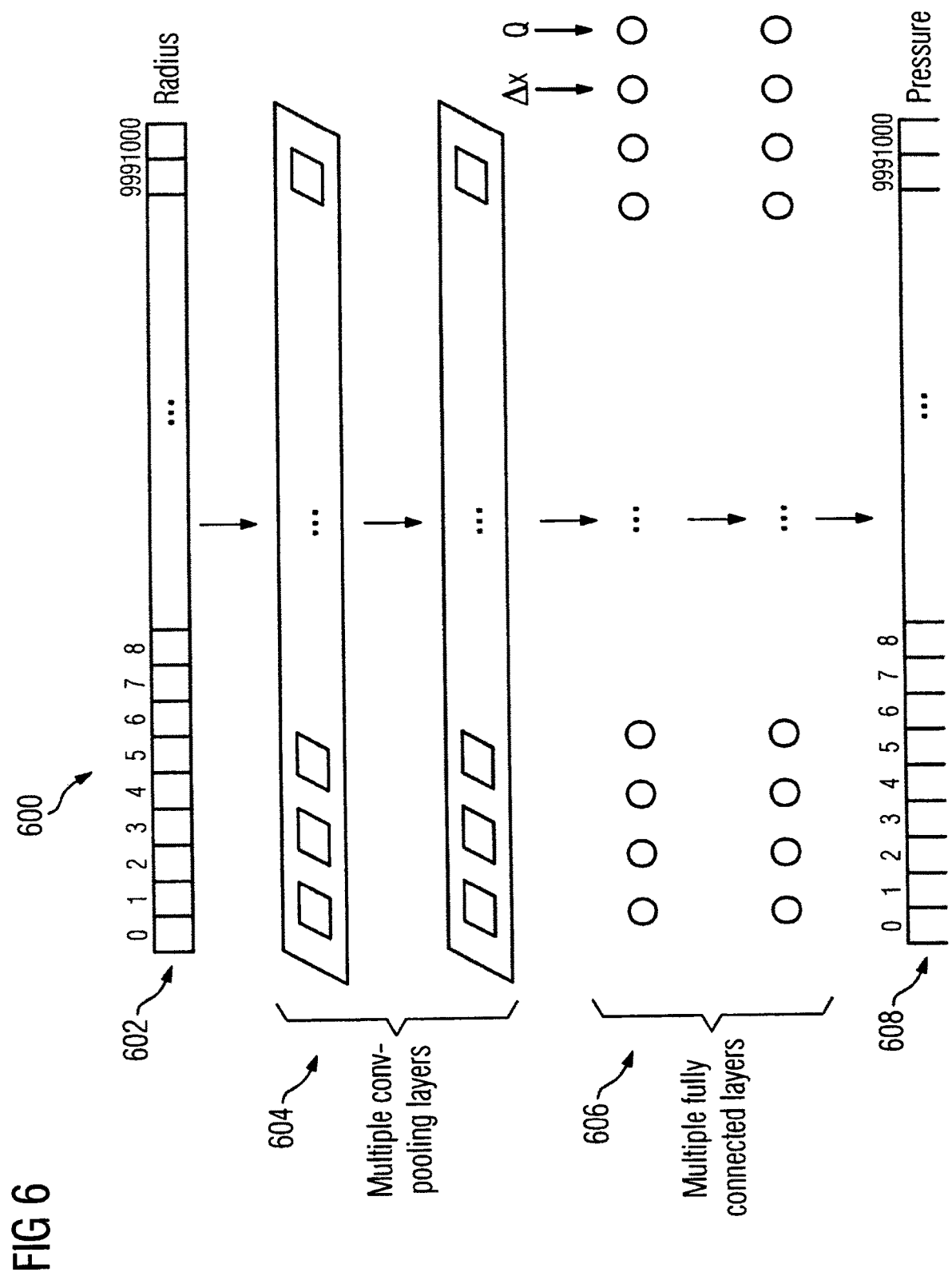
FIG. 6 illustrates an exemplary convolutional neural network (CNN) architecture for predicting pressure along a centerline of a coronary artery according to an embodiment of the present invention.

FIG. 6 illustrates an exemplary CNN architecture 600 for predicting pressure along a centerline of a coronary artery according to an embodiment of the present invention. In the CNN architecture 600 of FIG. 6, M=1, as only the radius is input as a feature at each centerline location, and N=1001 (i.e., the CNN 600 evaluates 1001 equally spaced locations along the vessel centerline). Additionally, the CNN 600 receives as input to the its fully connected layers the spacing between consecutive locations (Δx) along the centerline and the cycle averaged flow rate (Q). The M×N input array 602 including the radius values for each of the locations is input to the CNN 600. Multiple convolutional pooling layers 604 are used to generate relevant feature maps from the input array. Next, multiple fully connected layers 600 use these feature maps, and additionally the inputs given by the spacing between the locations Δx and the cycle average flow rate Q. Finally, a '1D image' 608 is generated as output containing the pressure values at all of the locations at which the radius was input.

In a possible implementation, the CNN can be used to predict time-varying hemodynamic results. In this case, an extra dimension is added to the output (and possibly to the input, e.g., if the radius is changing in time) representing the input/output information at each time step. The CNN can be trained based on a training database made up of synthetically generated vascular geometries and CFD simulations for each geometry that provide the ground truth spatial distribution of hemodynamic variables (e.g., pressure values). In the case of multiple coronary artery branches (bifurcations), the trained CNN is applied independently to each branch. The only geometrical configuration for which a separate model is required is for the case of bifurcation stenoses. According to an advantageous implementation, a separate CNN architecture can be trained to evaluate bifurcation stenoses cases and the CNN architecture for predicting pressure and/or vFFR for bifurcation stenoses can input radius information of all three branches, as well as additional contour radiuses, and other features of all of the branches.

Returning to FIG. 3, at step 308, post-treatment values of the hemodynamic quantity of interest are predicted along the branches of the coronary artery tree for each of a plurality of candidate treatment options. The treatment option candidates correspond to actual treatment options for treating the patient's coronary artery disease. For example, the treatment option candidates can be different PCI treatment options in which stents are placed at one or more locations in the coronary artery tree. The prediction of post-treatment vFFR (or other hemodynamic quantity) for each treatment option candidate results in a predicted post-treatment vFFR pullback curve for each treatment option candidate. Predicted post-treatment vFFR pullback curves can be generated for various treatment option candidates corresponding to various stenting arrangements to predict the effects of stenting in various combinations of the one or more lesions detected in the coronary artery tree, as well as to predict the effects of stenting with full lesion coverage versus spot stenting at various locations within a lesion. As described above, the estimated vFFR pullback curve computed in step 306 can be used to evaluate stenosis severity for each of the lesions in the coronary artery tree and assign a score to each lesion that characterizes the stenosis severity. For each of the treatment option candidates, the predicted post-treatment vFFR pullback curve can be used to predict the hemodynamic severity of the lesions after the treatment and determine a predicted post-treatment score for each lesion. The predicted post-treatment vFFR pullback curves and/or predicted post-treatment lesion scores for each of the treatment option candidates can be compared to each other and to the estimated pre-treatment pullback curve and lesion scores to evaluate the effects of the different treatment option candidate and select an optimal treatment option candidate for the patient.

In advantageous embodiments of the present invention, the post-treatment/post-PCI vFFR values are computed without modifying the patient-specific anatomical model of the coronary arteries to reflect each treatment. This is advantageous over existing techniques because modifying the patient-specific anatomical takes time and is computationally expensive and typically cannot be fully automated. Three embodiments are described herein for generating post-PCI scenarios and computing the predicted post-PCI vFFR for the post-PCI scenarios.

Figure 7:
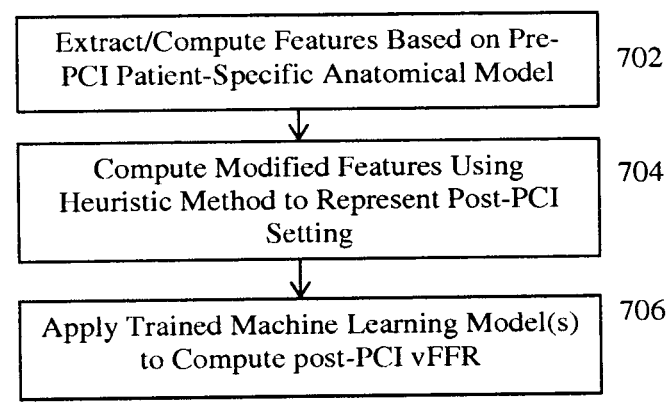
FIG. 7 illustrates a method for computing post-PCI vFFR values by directly computing post-PCI features according to an embodiment of the present invention.

In a first embodiment, features extracted from the pre-PCI anatomical model of the coronary arteries are directly modified to represent changes do to stenting in different post-PCI scenarios. FIG. 7 illustrates a method for computing post-PCI vFFR values by directly computing post-PCI features according to an embodiment of the present invention. As shown in FIG. 7, at step 702, features are extracted and/or computed based on the pre-PCI patient-specific anatomical model of the coronary arteries. The feature extraction in this step is performed as discussed above in step 304 of FIG. 3 and step 404 of FIG. 4. At step 704, modified features are computed from the extracted features to represent the post-PCI setting corresponding to a particular treatment option candidate. The features can be modified using a heuristic method to represent the post-PCI setting. In an exemplary implementation, the ischemic contribution score is modified for segments of the coronary artery in which stenting is to occur in the particular treatment option candidate. The ischemic contribution score can be modified using the following formula:

$$s = f_4(r(x))w_1 + f_s(r(x))w_1^2$$

where s is the ischemic contribution score, r(x) is the longitudinally varying vessel radius, w is the ischemic weight, and $f_4$ and $f_s$ are two operators which implement the effect of stenting on the ischemic contribution score. Furthermore, the ischemic weights of the branches containing the stenosis/stenoses to be stented may also be modified, as a result of a different effect on the total contribution score of the corresponding branch or as a result of a different interaction between the branches. At step 706, one or more trained machine learning models are used to compute post-PCI vFFR values along the coronary artery tree of the patient based on the modified features. For example, the machine learning model described in U.S. Pat. No. 9,349,178, which is incorporated herein in its entirety by reference, can be used to compute the post-PCI vFFR values based on the modified features or the cascaded machine learning models described above in connection with FIG. 4 may be used to compute the post-PCI vFFR values based on the modified features. Steps 704 and 706 are repeated for each treatment candidate option to generate predicted vFFR pullback curves for each treatment candidate option.

Figure 8:
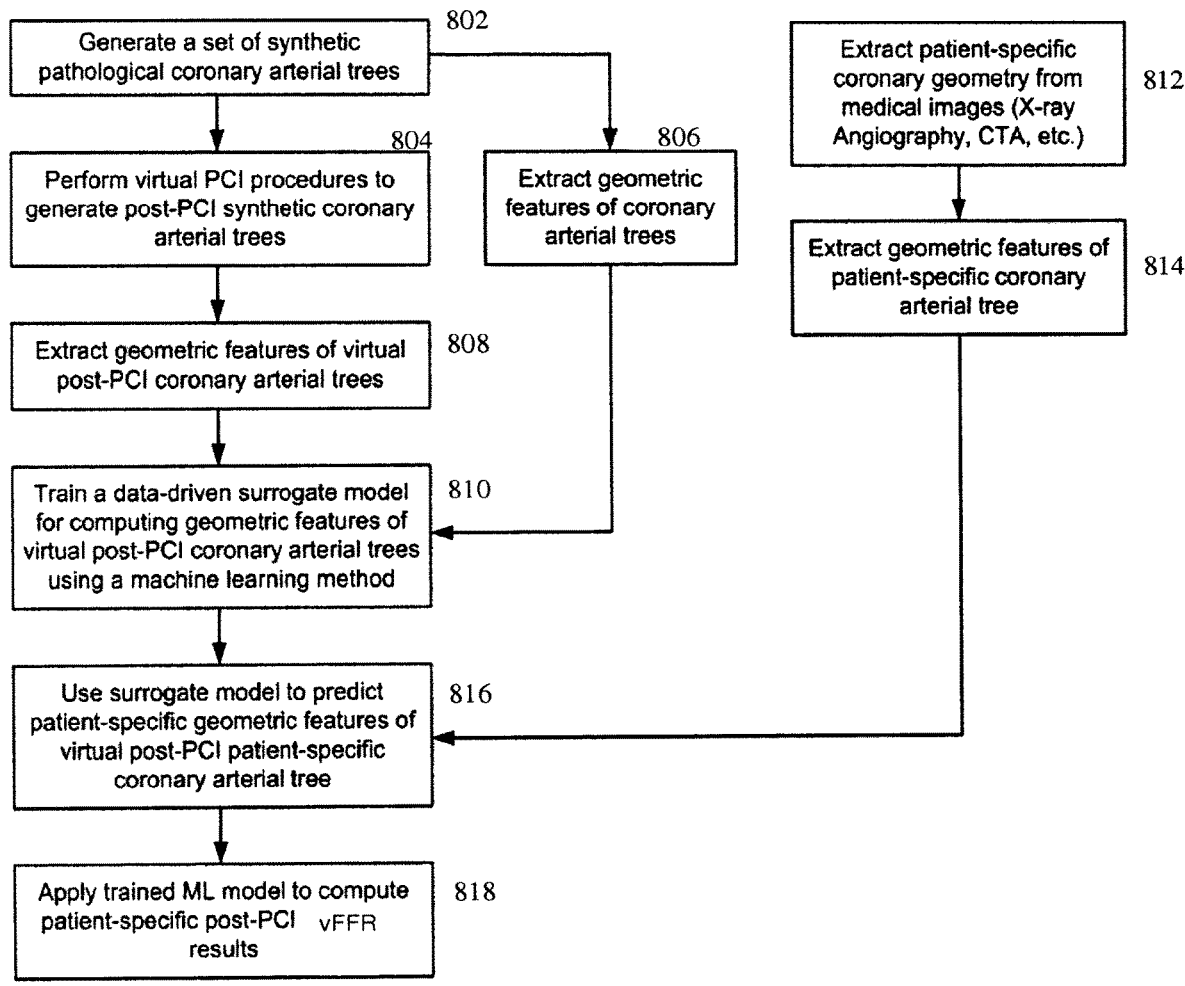
FIG. 8 illustrates a method of computing post-PCI vFFR values by using a machine learning model to compute post-PCI features according to an embodiment of the present invention.

In a second embodiment, a machine learning based method is used to predict features corresponding to the post-PCI anatomy for each treatment option. This machine-learning method can be based on the existence of a large database of synthetically generated pathological coronary arterial trees. FIG. 8 illustrates a method of computing post-PCI vFFR values by using a machine learning model to compute post-PCI features according to an embodiment of the present invention. The method of FIG. 8 uses a machine learning model to predict patient-specific geometric features of the post-PCI coronary arterial tree based on features extracted from the pre-PCI patient-specific coronary arterial tree anatomy without modifying the pre-PCI patient-specific anatomical model. In FIG. 8, steps 802-810 are performed in an offline training stage prior to receiving/acquiring new medical image data for a particular patient and steps 812-818 are performed in a prediction stage to predict post-PCI vFFR values for a particular patient from medical image data of the patient.

As shown in FIG. 8, in the training stage, at step 802, a set of synthetic pathological coronary arterial trees is generated. At step 804, for each of the synthetically generated coronary artery anatomical models, one or more synthetic post-PCI coronary anatomical models are generated by performing virtual PCI. At step 806, geometric features are extracted from the baseline (pre-PCI) synthetic coronary arterial trees, and at step 808, geometric features are extracted from the virtual post-PCI coronary arterial trees. At step 810, a data-driven surrogate model for computing geometric features virtual post-PCI coronary arterial trees is trained using one or more machine learning methods. In order to train the surrogate model, the geometric features extracted (in step 806) from the baseline synthetic coronary arterial trees are used as inputs to the surrogate model and geometric features extracted (in step 808) from the virtual post-PCI synthetic coronary arterial trees are used as ground truth outputs. The surrogate model is trained using a machine learning method to minimize a loss function between the ground truth post-PCI geometric features extracted in step 808 and the predicted post-PCI features output by the surrogate model over the set of training samples. Accordingly, the surrogate model is trained to learn a mapping between pre-PCI geometric features and post-PCI geometric features. The surrogate model can be implemented using a machine learning based regression model. Any type of machine learning method may be used to train the surrogate model. In an exemplary implementation, the surrogate model may be trained using a deep learning architecture.

Once the surrogate model is trained, the surrogate model is stored on a storage device or memory of a computer and is applied online in the prediction stage to predict post-PCI geometric features for newly received pre-PCI patient-data without having to explicitly generate a patient-specific post-PCI anatomical model. In the prediction stage, at step 812, patient-specific coronary geometry is extracted from medical images (e.g., X-ray Angiography, CTA, etc.) of the patient. At step 814, geometric features (pre-PCI) of the patient-specific coronary arterial tree are extracted. At step 816, the trained surrogate model is used to predict patient-specific geometric features of a virtual post-PCI patient-specific coronary arterial tree based on the extracted pre-PCI geometric features. The geometric features extracted from the pre-PCI patient-specific coronary anatomy are input to the trained surrogate model, and the trained surrogate model outputs predicted post-PCI geometric features without explicitly generating a post-PCI patient-specific anatomical model. At step 818, a trained machine-learning model is applied to compute patient-specific post-PCI vFFR values, resulting in a predicted post-PCI vFFR pullback curve. Once the predicted-post PCI geometric features are computed using the trained surrogate model, these features can be used to compute the hemodynamic metrics of interest corresponding to the post-PCI setting using the same machine learning model that is employed for computing the pre-PCI values. For example, the predicted post-PCI vFFR values (or other hemodynamic metric) can be predicted using the cascaded regression models, the trained RNN, or the trained CNN discussed above based on the predicted post-PCI geometric features output by the trained surrogate model. This can be performed for each of multiple treatment option candidates. In cases of anatomical models with multiple stenoses, the trained surrogate model may additionally use as a feature an index identifying the stenosis to be virtually treated in a given treatment option candidate. This information may be received as input from the user or may be automatically generated to cycle through multiple possible treatment options.

Figure 9:
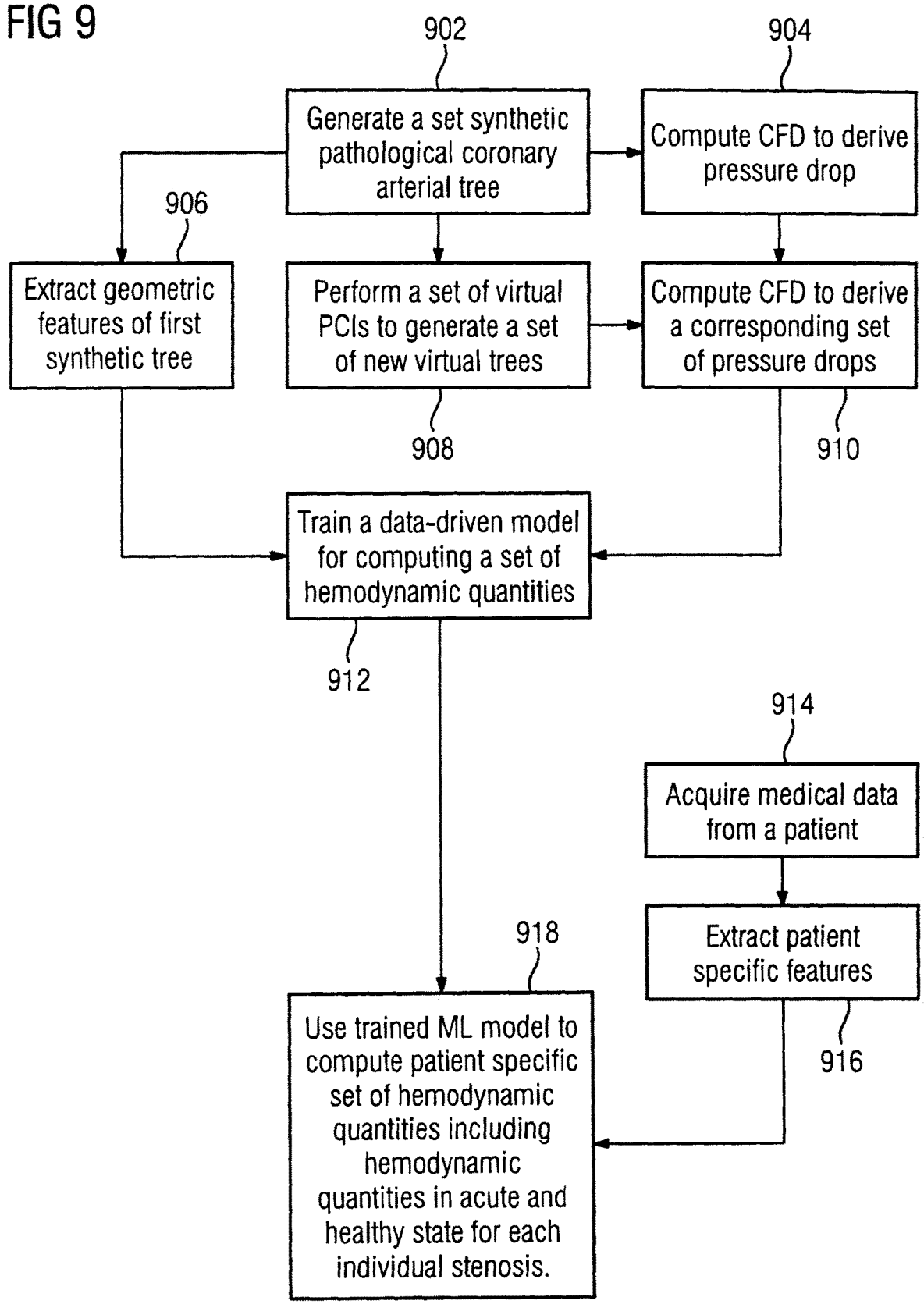
FIG. 9 illustrates a machine learning based method for computing post-PCI vFFR values based on pre-PCI features according to an embodiment of the present invention.

In a third embodiment, a machine learning based method is used to predict the post-PCI hemodynamic quantities (e.g., vFFR) for each treatment option candidate from the pre-PCI features extracted from medical image data. In this embodiment, instead of training a machine learning model that predicts features corresponding to the post-PCI setting as in the previous embodiment, a separate machine learning model is trained to directly predict the post-PCI hemodynamic quantities of interest (e.g., vFFR) from the pre-PCI features. This machine learning model may be trained using ground truth results extracted from CFD-based simulations performed on virtually treated synthetic coronary anatomical models. FIG. 9 illustrates a machine learning based method for computing post-PCI vFFR values based on pre-PCI features according to an embodiment of the present invention. The method of FIG. 9 uses a machine learning model to directly predict patient-post-PCI vFFR values based on features extracted from the pre-PCI patient-specific coronary arterial tree anatomy without modifying the pre-PCI patient-specific anatomical model. In FIG. 9, steps 902-912 are performed in an offline training stage prior to receiving/acquiring new medical image data for a particular patient and steps 914-918 are performed in a prediction stage to predict post-PCI vFFR values for a particular patient from medical image data of the patient.

As shown in FIG. 9, in the training stage, at step 902, a set of synthetic pathological coronary arterial trees is generated. At step 904, for each of the synthetically generated coronary artery anatomical models, one or more synthetic post-PCI coronary arterial trees are generated by performing a set of virtual PCIs. At step 906, CFD simulations are computed in the first (pre-PCI) synthetic coronary arterial trees to derive pressure drop, and at step 908, CFD simulations are performed in the set of virtual post-PCI coronary arterial trees to derive a corresponding set of pressure drops. At step 910, geometric features are extracted from the first (pre-PCI) synthetic coronary arterial trees. At step 912, a data-driven machine learning model for computing a set of post-PCI coronary hemodynamic quantities is trained using one or more machine learning methods. In order to train the machine learning model, the geometric features extracted (in step 910) from the baseline synthetic coronary arterial trees are used as inputs to the machine learning model and the pressure drops computed (in step 908) from the virtual post-PCI synthetic coronary arterial trees or hemodynamic quantities of interest (e.g., vFFR) computed from these pressure drops are used as ground truth outputs. The input geometric features can include the number and locations of the stenoses in each synthetic coronary artery tree. The set of pressure drops used to generate the ground truth outputs can include pressure drops corresponding to all possible PCI scenarios (e.g., all possible combinations of stenting one or more stenoses) for a given synthetic coronary artery tree.

The machine learning model is trained using a machine learning method to minimize a loss function between the ground truth post-PCI hemodynamic quantities computed in step 908 and the predicted post-PCI hemodynamic quantities output by the surrogate model over the set of training samples. Accordingly, the machine learning model is trained to learn a mapping between pre-PCI geometric features and post-PCI hemodynamic quantities, such as post-PCI vFFR or pressure-drop. The machine learning model can be implemented using a machine learning based regression model. Any type of machine learning method may be used to train the machine learning model. In an exemplary implementation, the machine learning model may be trained using a deep learning architecture.

Once the machine learning model is trained, the machine learning model is stored on a storage device or memory of a computer and is applied online in the prediction stage to predict post-PCI hemodynamic quantities for newly received pre-PCI patient-data without having to explicitly generate a patient-specific post-PCI anatomical model. In the prediction stage, at step 914, medical image data of a patient is acquired. At step 916, patient-specific features (pre-PCI) of the coronary arterial tree of the patient are extracted from the medical image data. The extracted patient-specific features include geometric features, as well as a number and location of the stenoses in the coronary artery tree, which can be determined by the detection of the lesions performed in step 306 of FIG. 3. At step 8918, the trained machine learning model is used to compute a patient-specific set of post-PCI hemodynamic quantities (e.g., vFFR), including hemodynamic quantities in acute and healthy states of each individual stenosis, based on the extracted pre-PCI patient-specific features. According to an advantageous implementation, based on the number and location of the stenoses in the coronary artery tree that are input as features to the trained machine learning model, the trained machine learning model can compute vFFR values (or other hemodynamic quantities) for all possible post-PCI scenarios (e.g., all possible combinations of stenting one or more stenoses) and thus automatically generate predicted vFFR pullback curves corresponding to all possible treatment option candidates.

Returning to FIG. 3, in one embodiment, the method of FIG. 3 proceeds from step 308 to step 312. That is, in one embodiment, the treatment prediction and guidance can be determined based on the predicted post-treatment values of the hemodynamic quantity of interest without performing step 310. In another embodiment, the method proceeds from step 308 to step 310, and then to step 312. At step 310, post-treatment scenarios corresponding to multiple treatment options for each lesion are generated and the treatment scenarios are scored based on hemodynamic significance and plaque stability. In an advantageous implementation, the multiple treatment options for a lesion correspond to "spot" stenting of the lesion at one or more locations within the lesion and full stenting of the lesion. Spot stenting/spot treatment refers to stenting a portion of a lesion less than the whole length of the lesion. In a possible embodiment, scoring of the lesions based on the vFFR values and the predicted post-PCI vFFR values computed in step 306 may be used to determine for which stenoses to perform PCI and scoring of the different treatment options for a particular stenosis based on hemodynamic significance and plaque stability performed in step 310 can be used to determine whether to perform complete stenting or spot stenting and where to perform spot stenting for that stenosis. In another possible embodiment, the predicted post-PCI vFFR values can be used together with the plaque stability/vulnerability index computed in step 310 to determine both which stenoses should be stented and what locations (spot stenting or full stenting) within each stenosis should be stented.

Given a patient-specific anatomical model of a coronary artery, as well as additional patient data, such as demographic data and blood biomarkers, plaque vulnerability can be estimated for a post-PCI scenario. A method of estimating plaque vulnerability can be implemented as follows. Medical data of the patient is acquired. The medical data can include the medical image data (e.g., CAT, X-ray Angiography, etc.), demographic data (e.g., age, gender, etc.), and blood biomarkers, as well as other types of medical data of the patient (e.g., non-invasive measures, such as heart, blood pressure, etc.). In a possible implementation, the blood biomarkers can include one or more of interleukin (IL), tumor necrosis factor-$\alpha$ (TNF-$\alpha$), monocyte chemoattractant protein-1 (MCP-1), soluble intercellular adhesion molecule-1 (sICAM), soluble vascular cell adhesion molecule (sVCAM), oxidized low density lipoprotein (oxLDL), lipoprotein associated phospholipase A2 (Lp-PLA2), glutathione peroxidase (GPx-1), myeloperoxidase (MPO), matrix metalloproteinases (MMPs), placental growth factor (PIGF), pregnancy-associated plasma protein-A (PAPP-A), soluble CD40 ligand (sCD40L), C-reactive protein (CRP), secretory type II phospholipase A2 (sPLA2), serum amyloid A (SAA), and white blood cell count, but the present invention is not limited thereto and other biomarkers may be used as well. Features of interest are extracted from the input medical data of the patient. The features of interest can include features of the vessel anatomical models from the medical images and other non-image features including demographic data features (age, gender, etc.) and the values for the blood biomarkers of the patient. Measures of interest related to the atherosclerotic plaque are predicted using a machine learning model trained based on known training data using a machine learning algorithm. These measures may include a plaque vulnerability index related to a specific lesion in a coronary artery or a global vulnerability index that represents a global risk of a cardiac event. The machine learning model can be implemented as a regression model trained using any machine learning algorithm. For example, in an advantageous implementation, a deep learning architecture can be used to train the machine learning model.

Figure 10:
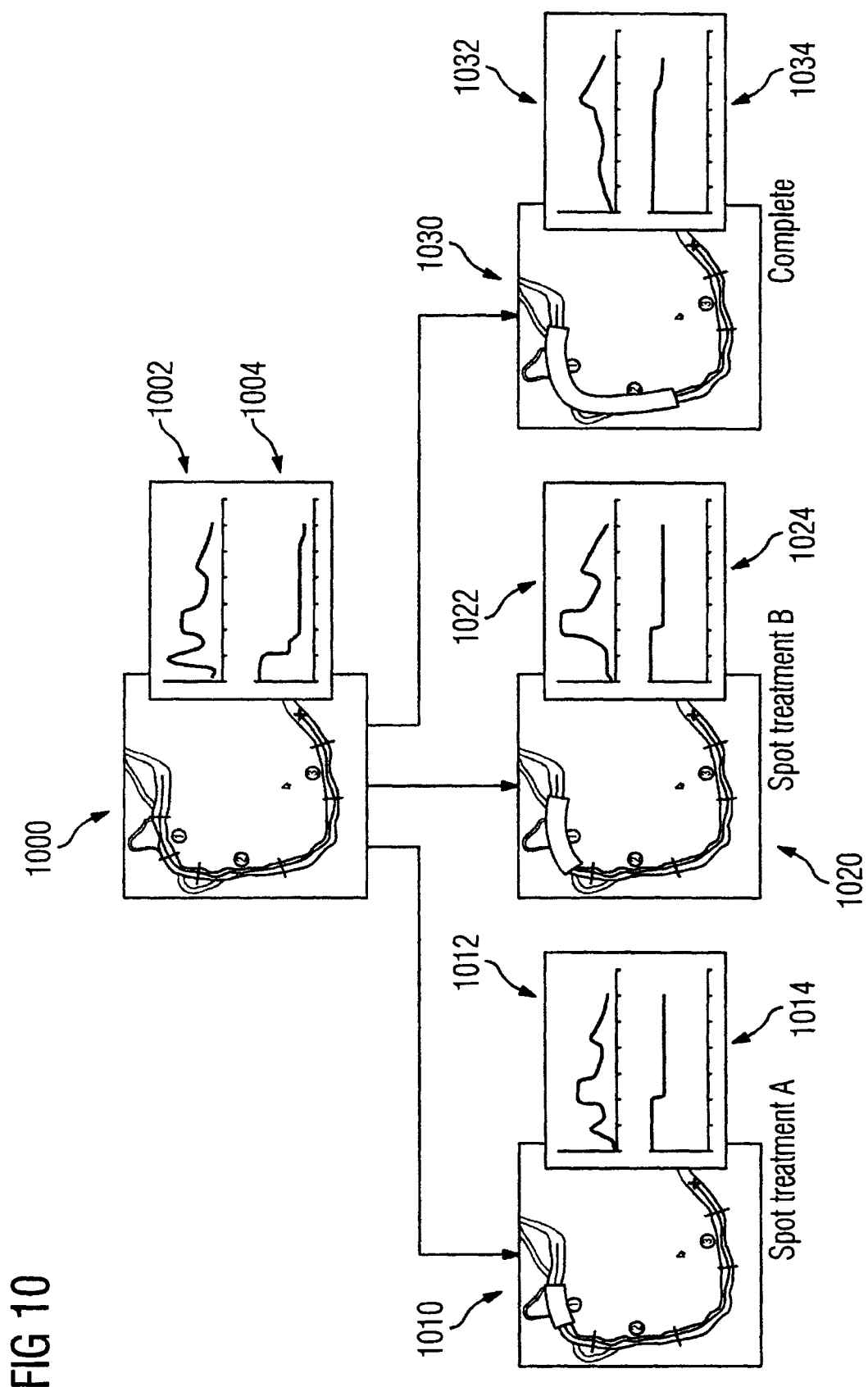
FIG. 10 illustrates an example of predicted plaque vulnerability indexes and post-PCI vFFR values for multiple post-PCI scenarios according to an embodiment of the present invention.

In an advantageous embodiment, a plaque vulnerability index is computed for each post-PCI scenario for a particular lesion. In an exemplary implementation, the plaque vulnerability index corresponds to a risk of a cardiovascular event (e.g., myocardial infarction, stent thrombosis/restenosis, etc.) related to the atherosclerotic plaque. The risk may be provided as a single score or as a segment-wise (likelihood that the considered vascular location will cause a cardiac event). FIG. 10 illustrates an example of predicted plaque vulnerability indexes and post-PCI vFFR values for multiple post-PCI scenarios according to an embodiment of the present invention. As shown in FIG. 10, image 1000 shows a pre-PCI angiographic view of a stenotic right coronary artery with three stenoses. The index of plaque vulnerability 1002 is computed along the centerline of the right coronary artery and displayed alongside the angiographic view 1000. The index of plaque vulnerability can be combined with an index of hemodynamic significance, such as vFFR. In FIG. 10, the vFFR pullback curve 1004 is also displayed the angiographic view 1000 together with stenosis markers that show the locations of the stenoses. Thanks to the real-time performance for the trained machine learning based models, the plaque vulnerability index and vFFR pullback curve can be predicted for multiple different therapy scenarios. In FIG. 10, images 1010, 1020, and 1030 show a three different post-PCI scenarios corresponding to three different treatment options for the stenoses in image 1000. The predicted plaque vulnerability index 1012, 1022, and 1032, and the predicted vFFR pullback curve 1014, 1024, and 1034 are also displayed for each of the post-PCI scenarios.

In FIG. 10, images 1010 and 1020 correspond to two different options for spot treatment ("Spot treatment A" and "Spot treatment B", respectively) with simulated stent placement in different locations and stents with different lengths (represented in images 1010 and 1020 by the mesh tube overlaid on the vessel) treating only the first stenotic segment. Image 1030 corresponds to a comprehensive treatment (complete coverage) for both the first and second stenotic segments. Other visual clues can be presented to the used rather the mesh overlay shown in FIG. 10 to indicate the positioning of the stent, such as stent markers indicating the proximal and distal end of the stent after placement. As shown in FIG. 10, the plaque vulnerability index 1012, 1022, and 1032 and the vFFR pullback curve 1014, 1024, and 1034 vary depending on the treatment option. In the example of FIG. 10, spot treatment A would resolve the flow limitation with the vFFR 1014 not becoming critical over the entire length of the coronary artery. In addition, spot treatment A would cause the plaque vulnerability index 1012 in the first stenosis to decrease as compared to the pre-PCI plaque vulnerability index 1002. However, due to increased blood flow in the vessel after PCI, spot treatment A would cause the plaque vulnerability index 1012 to increase for the second stenosis. This effect would not be mitigated by spot treatment B, which would only further reduce the plaque vulnerability index 1022 for the first stenosis. The complete coverage approach in image 1030 resolves the flow limitation, as shown by the predicted vFFR pullback curve 1034 and results in overall greater plaque stability (reduced plaque vulnerability), as shown by the predicted plaque vulnerability index 1032.

Based on the predicted vFFR pullback curve and the predicted plaque vulnerability index, the scoring of the different treatment scenarios can be performed in various ways. In a possible implementation, an exclusion criterion can be used to automatically exclude treatment options for which the vFFR downstream of the last stenosis would still be below a threshold value (e.g., vFFR<0.8). Among the remaining cases, a score can be assigned based on the integral average of the plaque vulnerability index along the length of the vessel with higher score being assigned to lower integral average.

To generate the candidate post-PCI scenarios, a dedicated machine learning algorithm (model) can be used that is trained for the purpose of generating variations of a given anatomical model including the presence of a stent. In one embodiment, this is achieved using generative adversarial networks (GANs). With this architecture, a generator neural network is trained to generate anatomical models (including the presence of stents) that have a realistic appearance, while an "adversarial" discriminator neural network is trained to distinguish real examples from artificial examples. Ground truth data could be provided in the form of anatomical models extracted from medical imagining data acquired post-PCI. Data could be provided, for example, in terms of a sequence of vector values corresponding to a sequence of properties associated with centerline points along the vessel. Examples of such properties can include the spatial coordinates of the centerline points, the radius of the vessel at the centerline points, a stenosis marker, and the presence of a stent (Boolean variable). In this case, both the generator and the discriminator networks could be recurrent neural networks (e.g., LSTMs). In alternative embodiment, deep reinforcement learning can be used to learn over time from user selections what should be the most desirable post-PCI scenario(s). The deep reinforcement learning can also consider technical feasibility and the physician's experience.

Modification of the anatomical model is however not required for the computation of the post-PCI scenarios. In particular, the methods discuss above can be used to estimate post-PCI conditions based purely on pre-PCI features.

Returning to FIG. 3, at step 312, a treatment prediction is output and treatment guidance is provided to the user. The treatment prediction can be output for multiple different treatment scenarios or an optimal treatment scenario can be automatically selected and output to the user. For example, after generating the post-PCI scenarios and the corresponding scores, the treatment scenarios and scores can be displayed on a display device. Other information, such as the predicted vFFR pullback curve and the predicted plaque vulnerability index curve for each treatment scenario (candidate) can also be displayed on the display device. If the generation of treatment scenarios is not constrained a priori, a large number of potential candidates can be produced. To reduce the number of options presented to the user, treatment candidates with a score below a given threshold can be automatically discarded. Alternatively, the post-treatment candidate with the highest score can be automatically selected and exclusively displayed to present that option to the user.

Figure 11:
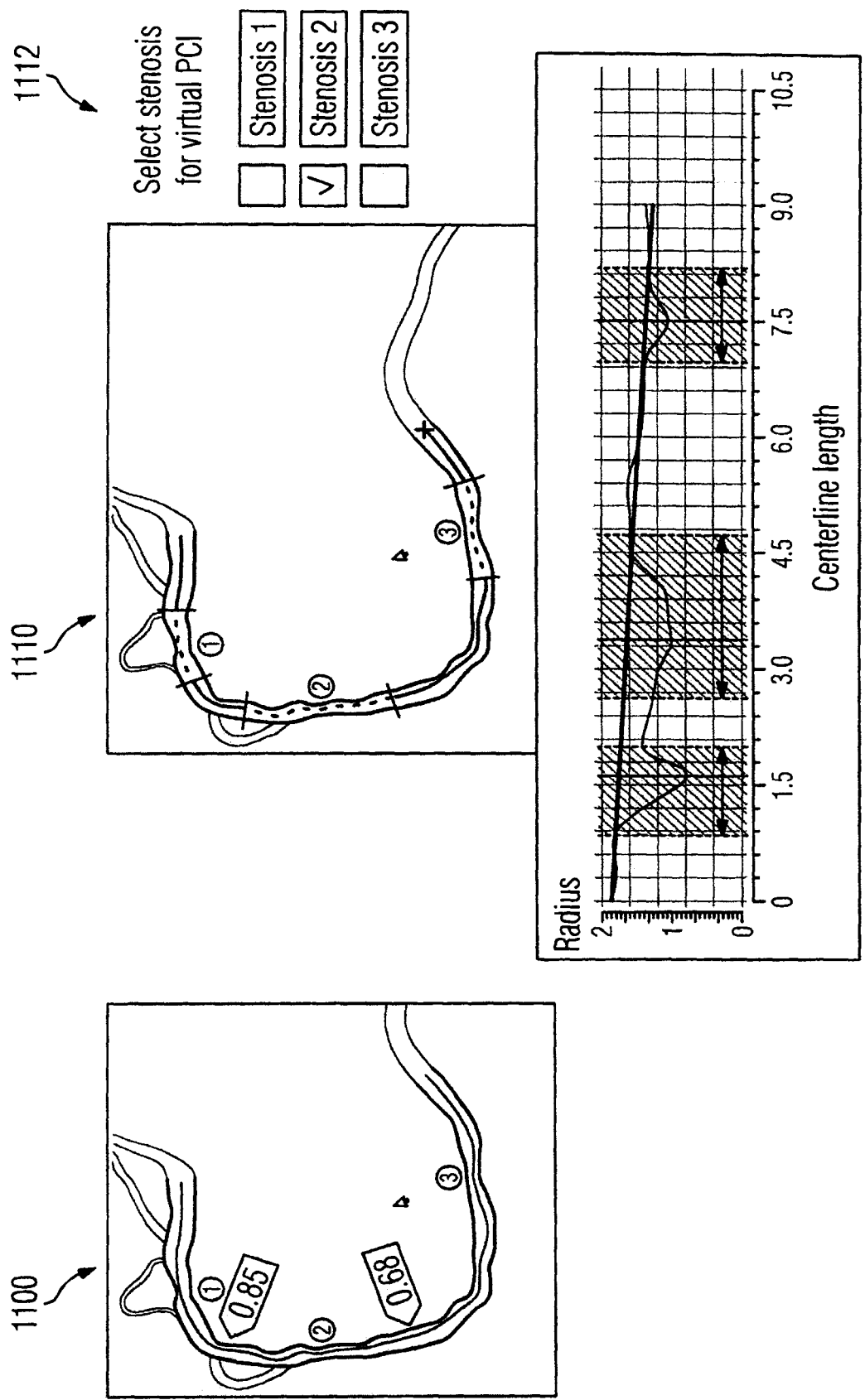
FIG. 11 illustrates an exemplary user interface for providing interactive guidance for treating coronary artery lesions according to an embodiment of the present invention.

In another embodiment, an interactive user interface may be presented to the user on a display device. The interactive user interface allows the user to select different possible treatment options and provides the score (and possible predicted vFFR and/or plaque vulnerability index) for the treatment options selected by the user. FIG. 11 illustrates an exemplary user interface for providing interactive guidance for treating coronary artery lesions according to an embodiment of the present invention. As shown in FIG. 11, an image 1100 showing the user the automatically detected stenosis segments is displayed on a display device together with a user interface 1110. The user interface 1110 includes controls 1112 that allow the user to select which stenosis segments should be considered for PCI. When the user inputs a selection of a which stenosis segments should be stented for a particular PCI treatment scenario, that PCI scenario can be automatically generated as scored (by predicting the post-PCI vFFR and/or the post-PCI plaque vulnerability index). The predicted vFFR pullback curve along the centerline can be displayed and/or selectable for different scenarios. The stenosis marker from that curve can be overlaid together with the centerline on the images. The centerline can be color coded to show segments where the vFFR is less than a threshold value (e.g., vFFR<0.8). The predicted plaque vulnerability index along the centerline can also be displayed and/or selectable for different scenarios.

Figure 12:
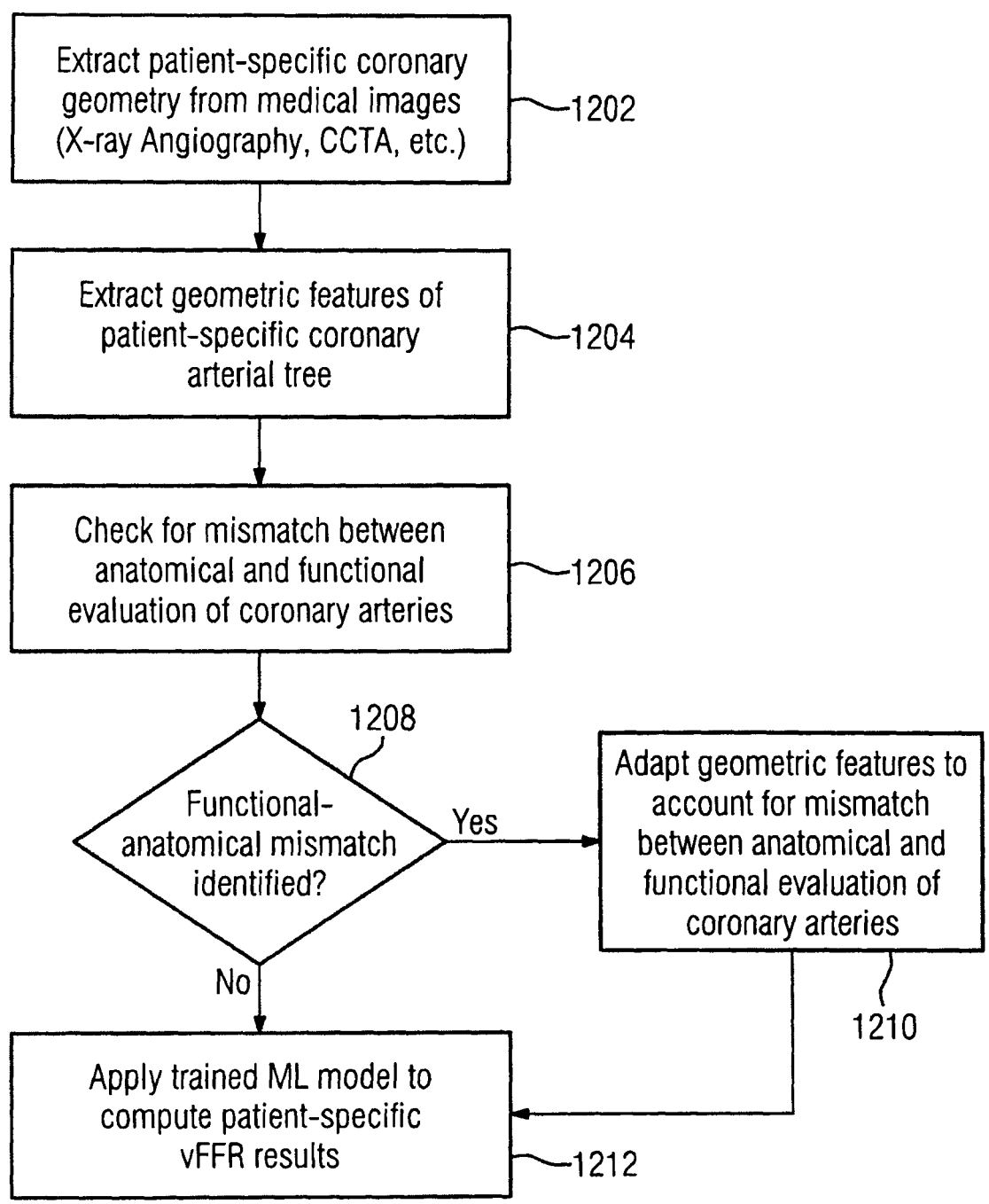
FIG. 12 illustrates a method for non-invasive computation of vFFR that accounts for a mismatch between anatomical and functional assessment of coronary artery lesions according to an embodiment of the present invention.

In an advantageous embodiment of the present invention, a modified method may be used to correctly diagnose patients with a mismatch between the anatomical and the functional evaluation of coronary lesions. Since the features used for computing the vFFR values are mainly based on anatomy, this embodiment is particularly advantageous for cases (such as diffuse lesions) for which the anatomy is not indicative of a functionally significant lesion. FIG. 12 illustrates a method for non-invasive computation of vFFR that accounts for a mismatch between anatomical and functional assessment of coronary artery lesions according to an embodiment of the present invention. As shown in FIG. 12, at step 1202, patient-specific coronary geometry is extracted from the medical images (e.g., X-ray Angiography, CCTA, etc.). At step 1204, geometric features of the patient-specific coronary artery tree are extracted. At step 1206, the method checks for a mismatch between the functional and anatomical evaluation of the coronary arteries. To identify a mismatch, different approaches may be used, depending on the type of medical images of the patient that are available.

For CCTA image data, diffuse disease may be identified based on the plaque burden present along the entire artery. Additionally, to be able to differentiate between positive remodeling (plaque deposits do not affect coronary lumen) and negative remodeling (plaque deposits induce decrease in coronary lumen), the size of the coronary artery lumen can be related to the myocardium being supplied by the corresponding coronary artery. To infer the type and extent of remodeling, this can be done specifically in comparison to a normal healthy artery.

For X-ray Angiography, a similar approach as for CCTA can be employed. However, since not all arteries are visible in the medical images, multiple projections may be used to reconstruct the entire arterial tree, and thus identify the myocardial regions supplied by each artery. Alternatively, the blood flow velocity may be determined using the contrast agent velocity as a surrogate marker, e.g., based on TIMI frame count, and this velocity may be compared to the blood flow velocity determined for a healthy artery, so as to identify the extent of diffuse disease. Only certain types of plaques can be reliably identified on coronary angiograms (e.g., calcified plaque).

At step 1208, it is determined whether a functional-anatomical mismatch has been identified. If a mismatch is identified, the method proceeds to step 1210. If no mismatch is identified, the method proceeds to step 1212. At step 1210, if a mismatch is identified, the geometric features are adapted to account for the mismatch between the anatomical and functional evaluation of the coronary arteries. For example, in a possible embodiment, the ischemic weight w of the coronary branches with the mismatch may be increased to account for the increased flow through that branch (using mathematical operators/formulas). In another embodiment, a trained machine learning model may be applied to perform the feature correction. Such a machine learning model can be trained based on synthetic and/or patient-specific data. In another alternative embodiment, training of a machine learning model may be performed directly on patient-specific data (e.g., including invasively measured FFR), in which case, the mismatch between the anatomical and the functional evaluation may be identified intrinsically from the medical images, and accounted for by the machine learning model.

At step 1212, a trained machine learning model is applied to compute the patient-specific vFFR results. For branches in which a mismatch is identified, the trained machine learning model inputs the adapted features generated in step 1210 instead of the original features extracted in step 1204.

In an embodiment of the present invention, the above described methods for non-invasive assessment and therapy guidance for coronary artery disease can be performed using a combine onsite-offsite analysis. For example, the onsite analysis can focus on the current patient state (i.e., diagnosis) and the offsite analysis can focus on the future evolution of the patient's coronary artery lesions. The two analyses may be performed simultaneously or subsequently. Such as setting would be advantageous, for example, if the decisions need to be taken while performing a medical procedure (e.g., during cathlab catheterization). In this case, the diagnosis needs to be performed in near real-time to not prolong the duration of the procedure, using an onsite algorithm. The patient evolution prediction can also be performed using more complex tools (e.g., also employing computational modeling based methods that perform three-dimensional blood flow computations). These results can then be used to guide long-term treatment of the patient, timing of recurrent medical examinations, etc.

In a possible embodiment, the predicted post-PCI scenarios and corresponding scores can be adapted based on available measurements taken from the patient at the time of intervention. For example, in the case of multiple lesions, the above described method may suggest treatment of one of the lesions, providing predicted vFFR in post-PCI conditions for that lesion. An invasive FFR measurement can be performed after the actual PCI procedure to verify removal of the flow limiting lesion. The measured FFR value is then compared with the predicted post-PCI vFFR. If the two values are not the same, the predicted vFFR for the other stenoses can then be updated using the measured FFR as an additional input. Methods for automatic adaption of vFFR based on available measurements are described in greater detail in U.S. Pat. No. 9,349,178, which is incorporated herein in its entirety by reference.

Figure 13:
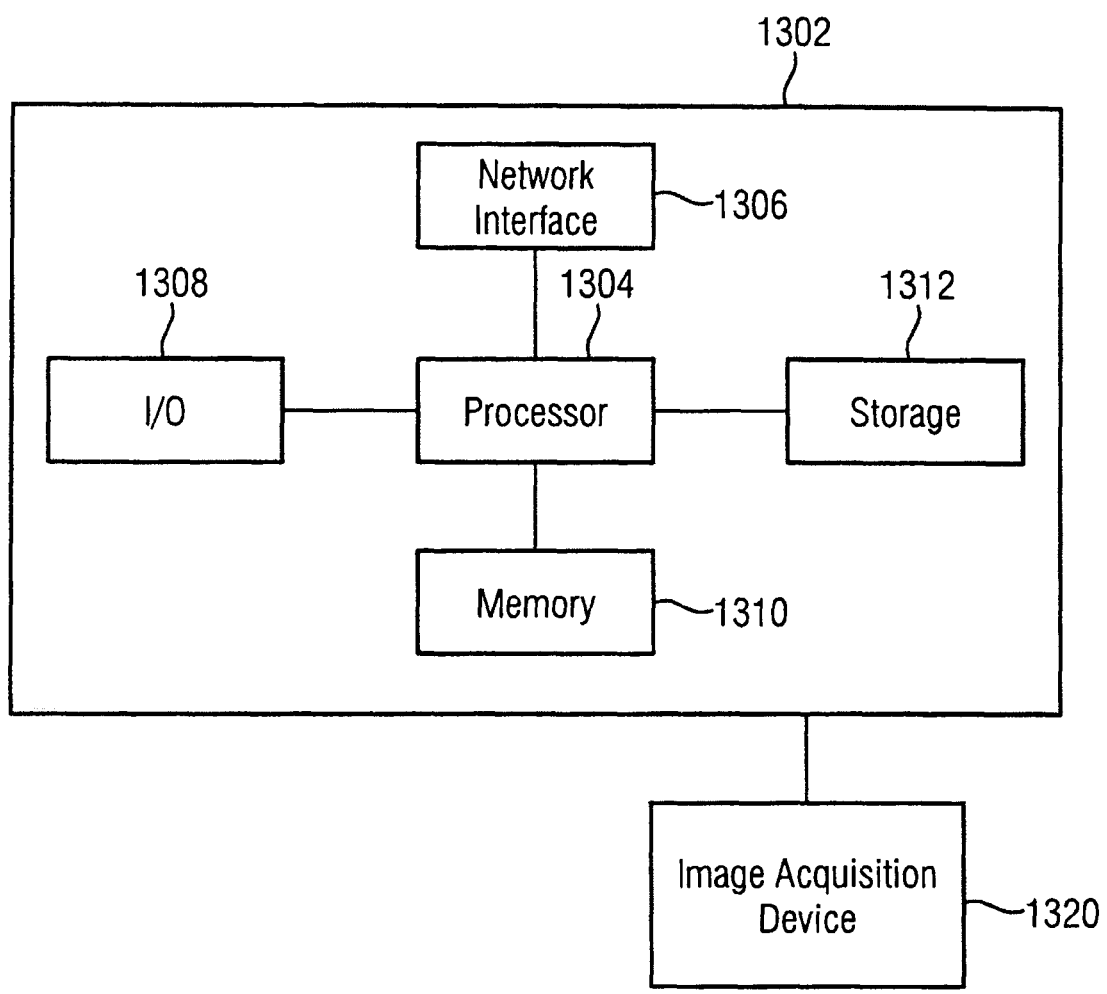
FIG. 13 is a high-level block diagram of a computer capable of implementing the present invention.

The above-described methods can be implemented on one or more computers using computer processors, memory units, storage devices, computer software, and other components. A high-level block diagram of such a computer is illustrated in FIG. 13. Computer 1302 contains a processor 1304, which controls the overall operation of the computer 1302 by executing computer program instructions which define such operation. The computer program instructions may be stored in a storage device 1312 (e.g., magnetic disk) and loaded into memory 1310 when execution of the computer program instructions is desired. Thus, the steps of the methods of FIGS. 3, 4, 7, 8, 9, and 12 may be defined by the computer program instructions stored in the memory 1310 and/or storage 1312 and controlled by the processor 1304 executing the computer program instructions. An image acquisition device 1320, such as a CT scanning device, X-ray scanning device, C-arm image acquisition device, MR scanning device, Ultrasound device, etc., can be connected to the computer 1302 to input image data to the computer 1302. It is possible to implement the image acquisition device 1320 and the computer 1302 as one device. It is also possible that the image acquisition device 1320 and the computer 1302 communicate wirelessly through a network. The computer 1302 also includes one or more network interfaces 1306 for communicating with other devices via a network. The computer 1302 also includes other input/output devices 1308 that enable user interaction with the computer 1302 (e.g., display, keyboard, mouse, speakers, buttons, etc.). One skilled in the art will recognize that an implementation of an actual computer could contain other components as well, and that FIG. 13 is a high level representation of some of the components of such a computer for illustrative purposes.

In one embodiment, the computer that performs one or more of the above described methods may be integrated into a medical image scanner (image acquisition device). In another embodiment, the computer that performs one or more of the above described methods may be a mobile device, such as a smart phone or tablet. In another embodiment, the computer that performs one or more of the above described methods may be part of a patient monitoring system.

In another embodiment, one or more of the above described methods may be implemented in network-based cloud computing system. In such a network-based cloud computing system, a server communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. Certain steps of the above described methods may be performed by a server or by other computers/processors in the network-based cloud-computing system. Certain steps of the above described methods may be performed locally by a client computer in a network-based cloud computing system. The steps of the above described methods may be performed by one or more devices in the network-based cloud-computing system or by a local client computer in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for non-invasive assessment and therapy planning for coronary artery disease from medical image data of a patient, comprising:
    extracting geometric features from medical image data representing at least a portion of a coronary artery tree of the patient;
    detecting one or more lesions in the coronary artery tree of the patient and computing a hemodynamic quantity of interest at a plurality of points along the coronary artery tree including multiple points within each of the one or more lesions based on the extracted geometric features using a first machine learning model, resulting in an estimated pullback curve for the hemodynamic quantity of interest;
    predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options; and
    displaying a visualization of a treatment prediction for at least one of the candidate treatment options for the patient.

2. The method of claim 1, wherein the first machine learning model comprises a first trained regression model and a second trained regression model, and detecting one or more lesions in coronary artery tree of the patient and computing a hemodynamic quantity of interest at a plurality of points along the coronary artery tree including multiple points within each of the one or more lesions based on the extracted geometric features using a first machine learning algorithm, resulting in an estimated pullback curve for the hemodynamic quantity of interest, comprises:
    computing the hemodynamic quantity of interest at points along healthy segments of the coronary artery tree using the first trained regression model; and
    computing the hemodynamic quantity of interest at the multiple points within each of the one or more lesions using the second trained regression model.

3. The method of claim 2, wherein computing the hemodynamic quantity of interest at the multiple points within each of the one or more lesions using the second trained regression model comprises, for each of the one or more lesions:
    computing a total pressure drop feature for the lesion based on values of hemodynamic quantity of interest proximal and distal to lesion computed by the first trained regression model;
    inputting the total pressure drop feature, features characterizing the entire lesion, and features characterizing the multiple points within the lesion to the second trained regression model; and
    computing the hemodynamic quantity of interest at the multiple points within the lesion based on the total pressure drop feature, the features characterizing the entire lesion, and the features characterizing the multiple points within the lesion to the second trained regression model using the second trained regression model.

4. The method of claim 1, wherein the first machine learning model comprises a trained recurrent neural network (RNN), and detecting one or more lesions in coronary artery tree of the patient and computing a hemodynamic quantity of interest at a plurality of points along the coronary artery tree including multiple points within each of the one or more lesions based on the extracted geometric features using a first machine learning algorithm, resulting in an estimated pullback curve for the hemodynamic quantity of interest, comprises:
    sequentially inputting local features for each of a plurality of centerline points along a centerline of the coronary artery tree to the trained RNN; and
    for each of the plurality of centerline points along the centerline of the coronary artery tree, computing the hemodynamic quantity of interest at that centerline point using the trained RNN by updating an internal state of the RNN based on the local features input for that centerline point and computing the hemodynamic quantity of interest at that centerline point based on the updated internal state of the RNN.

5. The method of claim 1, wherein the first machine learning model comprises a trained convolutional neural network (CNN), and detecting one or more lesions in coronary artery tree of the patient and computing a hemodynamic quantity of interest at a plurality of points along the coronary artery tree including multiple points within each of the one or more lesions based on the extracted geometric features using a first machine learning algorithm, resulting in an estimated pullback curve for the hemodynamic quantity of interest, comprises:
    for each of one or more branches of the coronary artery tree, inputting one or more local geometric features extracted at each of a plurality of equal spaced locations along the branch to the trained CNN as an M×N array, where N is a number of the equally spaced locations and M is a number of local geometric features input for each of the equally spaced locations, and computing the hemodynamic quantity of interest at each of a plurality of equally spaced locations along the branch based on the input array of local features using the trained CNN.

6. The method of claim 5, wherein the CNN inputs a radius value at each of the plurality of equally spaced locations and outputs a pressure value at each of the plurality of equally spaced locations.

7. The method of claim 1, wherein each of the one or more candidate treatment options corresponds to a candidate percutaneous coronary intervention (PCI) treatment, and predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options, comprises:
inputting the extracted geometric features to a second trained machine learning model;
predicting patient-specific post-PCI geometric features for each of the one or more candidate PCI treatments based on the input geometric features using the second trained machine learning model; and
predicting, for each of the one or more candidate PCI treatments, post-PCI values for the hemodynamic quantity of interest at the plurality of points along the coronary artery tree including the multiple points within each of the one or more lesions based on the predicted patient-specific post-PCI geometric features using the first machine learning model.

8. The method of claim 1, wherein each of the one or more candidate treatment options corresponds to a candidate percutaneous coronary intervention (PCI) treatment, and predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options, comprises:
inputting the extracted geometric features, a number of the lesions detected in the coronary artery tree of the patient, and locations of the lesions detected in the coronary artery tree of the patient to a second trained machine learning model; and
predicting, for each of one or more candidate PCI treatments corresponding to respective possible combinations of stenting at the detected lesions in the coronary artery tree, post-PCI values for the hemodynamic quantity of interest at the plurality of points along the coronary artery tree including the multiple points within each of the one or more lesions based on the input extracted geometric features using the second trained machine learning model.

9. The method of claim 1, wherein each of the one or more candidate treatment options corresponds to a candidate percutaneous coronary intervention (PCI) treatment, and the method further comprises:
predicting, for each of the one or more candidate PCI treatments, a plaque vulnerability index using a second trained machine learning model based on the geometric features corresponding to post-PCI anatomy for each of the one or more candidate PCI treatments and other features including one or more of demographic features or blood biomarkers.

10. The method of claim 9, wherein predicting, for each of the one or more candidate PCI treatments, a plaque vulnerability index using a second trained machine learning model based on the geometric features corresponding to post-PCI anatomy for each of the one or more candidate PCI treatments and other features including one or more of demographic features or blood biomarkers comprises:
predicting, for each of the one or more candidate PCI treatments, the plaque vulnerability index at the plurality of points along the coronary artery tree including the multiple points within each of the one or more lesions using the second trained machine learning model, resulting in a respective predicted plaque vulnerability index curve for each of the one or more candidate PCI treatments, wherein the plaque vulnerability index at each point corresponds to a likelihood that a vascular location will cause a cardiovascular event.

11. The method of claim 10, wherein each of the one or more candidate PCI treatments includes one or more stenting locations, and displaying a visualization of a treatment prediction for at least one of the candidate treatment options for the patient comprises:
displaying, for at least one of the candidate PCI treatments, an image showing at least a portion of the coronary artery tree of the patient with a visual representation of a stent overlaid on the coronary artery at the one or more stenting locations for the candidate PCI treatment, the predicted plaque vulnerability index curve for the candidate PCI treatment, and the predicted post-treatment pullback curve for the hemodynamic quantity of interest for the candidate PCI treatment.

12. The method of claim 9, further comprising:
scoring the one or more candidate PCI treatments based on the predicted post-treatment values of the hemodynamic quantity of interest and the predicted plaque vulnerability index for each of the one or more candidate PCI treatments.

13. The method of claim 12, wherein scoring the one or more candidate PCI treatments based on the predicted post-treatment values of the hemodynamic quantity of interest and the predicted plaque vulnerability index for each of the one or more candidate PCI treatments comprises:
automatically excluding all candidate PCI treatments for which the predicted post-treatment values of the hemodynamic quantity of interest fall below a threshold value; and
assigned a score to each of the remaining candidate PCI treatments based on the integral average of the predicted plaque vulnerability index.

14. The method of claim 9, wherein the one or more candidate PCI treatments include multiple stenting scenarios for stenting at least one of the lesions, including spot stenting at one or more locations within the lesion and complete stenting of the lesion.

15. The method of claim 14, further comprising:
generating post-PCI scenarios corresponding to each of the one or more candidate PCI treatments using a third trained machine learning model, wherein the third trained machine learning model is trained in a generative adversarial network (GAN).

16. The method of claim 1, further comprising:
prior to detecting the one or more lesions in coronary artery tree and computing the hemodynamic quantity of interest at the plurality of points along the coronary artery tree including the multiple points within each of the one or more lesions based on the extracted geometric features using a first machine learning model,
identifying a mismatch between an anatomical and functional evaluation in at least one branch of the coronary artery tree, and modifying the extracted geometric features in the at least one branch of the coronary artery tree to correct the mismatch between the anatomical and functional evaluation.

17. An apparatus for non-invasive assessment and therapy planning for coronary artery disease from medical image data of a patient, comprising:
means for extracting geometric features from medical image data representing at least a portion of a coronary artery tree of the patient;
means for detecting one or more lesions in the coronary artery tree of the patient and computing a hemodynamic quantity of interest at a plurality of points along the coronary artery tree including multiple points within each of the one or more lesions based on the extracted geometric features using a first machine learning model, resulting in an estimated pullback curve for the hemodynamic quantity of interest;
means for predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options; and
means for displaying a visualization of a treatment prediction for at least one of the candidate treatment options for the patient.

18. The apparatus of claim 17, wherein each of the one or more candidate treatment options corresponds to a candidate percutaneous coronary intervention (PCI) treatment, and the apparatus further comprises:
means for predicting, for each of the one or more candidate PCI treatments, a plaque vulnerability index using a second trained machine learning model based on the geometric features corresponding to post-PCI anatomy for each of the one or more candidate PCI treatments and other features including one or more of demographic features or blood biomarkers.

19. The apparatus of claim 18, further comprising:
means for scoring the one or more candidate PCI treatments based on the predicted post-treatment values of the hemodynamic quantity of interest and the predicted plaque vulnerability index for each of the one or more candidate PCI treatments.

20. The apparatus of claim 17, further comprising:
means for identifying a mismatch between an anatomical and functional evaluation in at least one branch of the coronary artery tree; and
and means for modifying the extracted geometric features in the at least one branch of the coronary artery tree to correct the mismatch between the anatomical and functional evaluation.

21. A non-transitory computer readable medium storing computer program instructions for non-invasive assessment and therapy planning for coronary artery disease from medical image data of a patient, the computer program instructions when executed by a processor cause the processor to perform operations comprising:
extracting geometric features from medical image data representing at least a portion of a coronary artery tree of the patient;
detecting one or more lesions in the coronary artery tree of the patient and computing a hemodynamic quantity of interest at a plurality of points along the coronary artery tree including multiple points within each of the one or more lesions based on the extracted geometric features using a first machine learning model, resulting in an estimated pullback curve for the hemodynamic quantity of interest;
predicting post-treatment values for the hemodynamic quantity of interest at the plurality of points along the coronary artery tree including the multiple points within each of the one or more lesions for each of one or more candidate treatment options for the patient, resulting in a respective predicted post-treatment pullback curve for the hemodynamic quantity of interest for each of the one or more candidate treatment options; and
displaying a visualization of a treatment prediction for at least one of the candidate treatment options for the patient.

22. The non-transitory computer readable medium of claim 21, wherein each of the one or more candidate treatment options corresponds to a candidate percutaneous coronary intervention (PCI) treatment, and the operations further comprise:
predicting, for each of the one or more candidate PCI treatments, a plaque vulnerability index using a second trained machine learning model based on the geometric features corresponding to post-PCI anatomy for each of the one or more candidate PCI treatments and other features including one or more of demographic features or blood biomarkers.

23. The non-transitory computer readable medium of claim 22, wherein the operations further comprise:
scoring the one or more candidate PCI treatments based on the predicted post-treatment values of the hemodynamic quantity of interest and the predicted plaque vulnerability index for each of the one or more candidate PCI treatments.

24. The non-transitory computer readable medium of claim 21, wherein the operations further comprise:
prior to detecting the one or more lesions in coronary artery tree and computing the hemodynamic quantity of interest at the plurality of points along the coronary artery tree including the multiple points within each of the one or more lesions based on the extracted geometric features using a first machine learning model,
identifying a mismatch between an anatomical and functional evaluation in at least one branch of the coronary artery tree, and modifying the extracted geometric features in the at least one branch of the coronary artery tree to correct the mismatch between the anatomical and functional evaluation.

* * * * *